US009848804B2

(12) United States Patent
Ohkoshi et al.

(10) Patent No.: US 9,848,804 B2
(45) Date of Patent: Dec. 26, 2017

(54) SENSOR INSERTION DEVICE AND SENSOR INSERTION METHOD

(71) Applicant: Terumo Kabushiki Kaisha, Tokyo (JP)

(72) Inventors: Takahiro Ohkoshi, Kanagawa (JP); Atsushi Matsumoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 487 days.

(21) Appl. No.: 14/663,297

(22) Filed: Mar. 19, 2015

(65) Prior Publication Data

US 2015/0190076 A1    Jul. 9, 2015

Related U.S. Application Data

(63) Continuation of application No. PCT/JP2012/074442, filed on Sep. 24, 2012.

(51) Int. Cl.
*A61B 5/145* (2006.01)
*A61B 5/1473* (2006.01)
*A61B 5/00* (2006.01)

(52) U.S. Cl.
CPC ........ *A61B 5/14503* (2013.01); *A61B 5/1473* (2013.01); *A61B 5/14532* (2013.01);
(Continued)

(58) Field of Classification Search
CPC ... A61B 5/145; A61B 5/14503; A61B 5/1459; A61B 5/1473; A61B 5/1486; A61B 5/14865; A61B 5/1455; A61B 5/14532
See application file for complete search history.

(56) References Cited

U.S. PATENT DOCUMENTS 6,560,471 B1 * 5/2003 Heller ............... A61B 5/14532
600/309
2007/0249922 A1 * 10/2007 Peyser ............. A61B 5/14532
600/365
(Continued)

FOREIGN PATENT DOCUMENTS

JP    2003-527138 A    9/2003
JP    2004-520898 A    7/2004
(Continued)

OTHER PUBLICATIONS

Extended European Search Report issued in European Patent Application No. 12884951.0 dated Apr. 22, 2016.
(Continued)

*Primary Examiner* — Eric Winakur
*Assistant Examiner* — Chu Chuan (JJ) Liu
(74) *Attorney, Agent, or Firm* — Foley & Lardner LLP

(57) ABSTRACT

A sensor insertion device for inserting a detection element of a sensor configured to measure biological information of a subject into the body of the subject includes a device body; a data process unit attached to the device body, a movement mechanism detachably attached to the device body, the movement mechanism being configured to move the detection element together with an insertion needle configured to be stuck into the body of the subject to insert the detection element and the insertion needle into the body of the subject; and a displacement preventing member.

15 Claims, 26 Drawing Sheets

(52) U.S. Cl.
 CPC .......... *A61B 5/6849* (2013.01); *A61B 5/0031* (2013.01); *A61B 2560/063* (2013.01)

(56) References Cited

U.S. PATENT DOCUMENTS

| | | | | |
|---|---|---|---|---|
| 2008/0114280 A1* | 5/2008 | Stafford | ............. | A61B 5/14532 604/19 |
| 2008/0319414 A1* | 12/2008 | Yodfat | ................. | A61B 5/6849 604/506 |
| 2010/0217105 A1* | 8/2010 | Yodfat | ............... | A61B 5/14503 600/365 |
| 2010/0324403 A1* | 12/2010 | Brister | ............... | A61B 5/14532 600/365 |
| 2011/0178461 A1* | 7/2011 | Chong | ............... | A61B 17/3415 604/151 |

FOREIGN PATENT DOCUMENTS

| | | |
|---|---|---|
| JP | 2008-506468 A | 3/2008 |
| JP | 2010-538745 A | 12/2010 |
| WO | WO-99/33504 A1 | 7/1999 |
| WO | WO-02/058537 A2 | 8/2002 |
| WO | WO-2006/017358 A1 | 2/2006 |
| WO | WO-2009/035773 A1 | 3/2009 |

OTHER PUBLICATIONS

First Office Action issued in Chinese Patent Application No. 201280075570.6 dated Apr. 6, 2016.
International Search Report issued in International Patent Application No. PCT/JP2012/074442 dated Oct. 23, 2012.

* cited by examiner

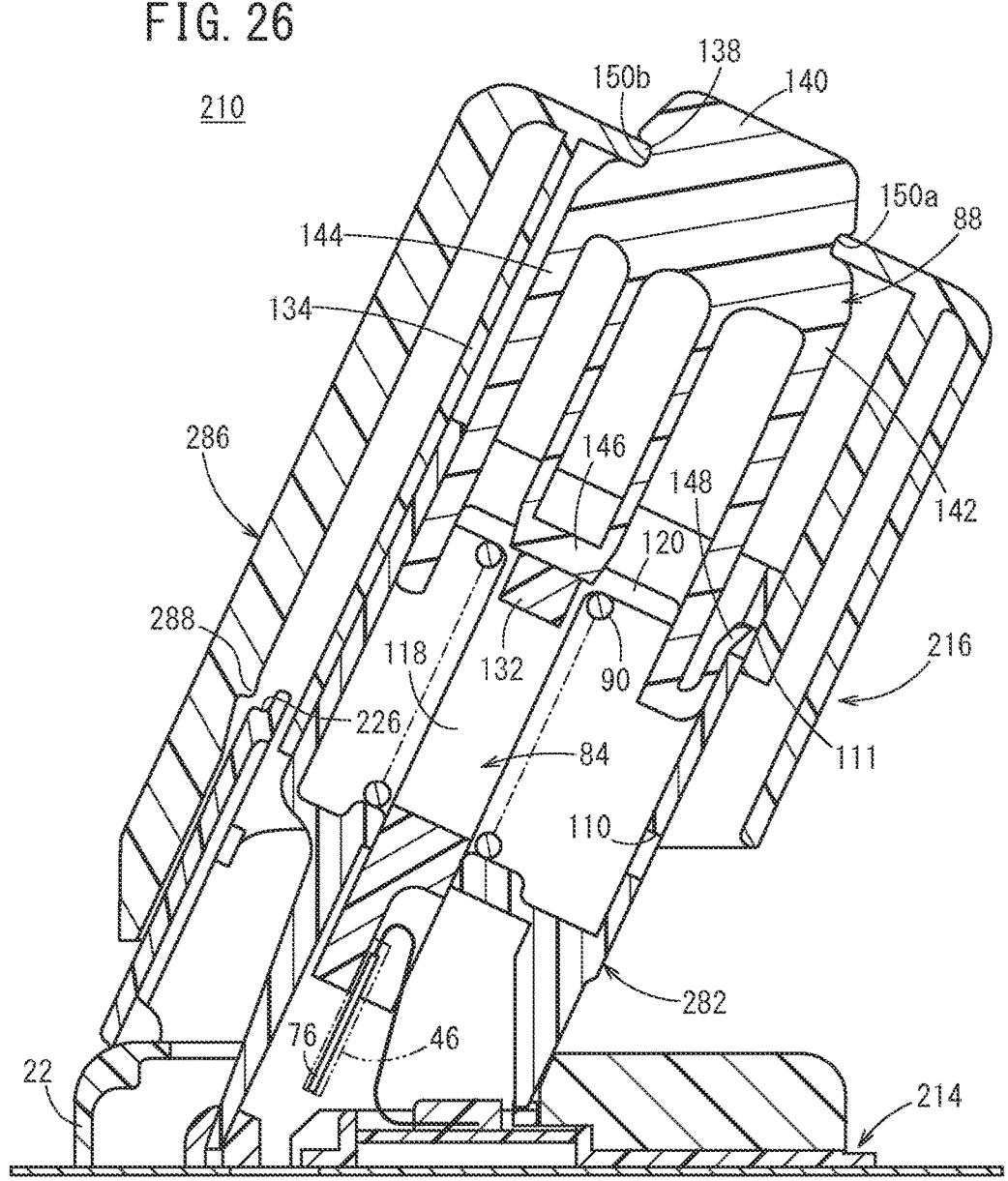

SENSOR INSERTION DEVICE AND SENSOR INSERTION METHOD

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/074442 filed on Sep. 24, 2012, the entire contents of which is hereby incorporated by reference in its entirety.

BACKGROUND

Technical Field

The present disclosure relates to a sensor insertion device which inserts a detection element of a sensor which measures biological information of a subject (patient) into a body of the subject and a sensor insertion method.

Background Art

An analyte (e.g., glucose or pH, cholesterol, or protein) in the blood or body fluid of a patient (subject) has been detected by a sensor inserted or implanted in the body of the patient. A sensor insertion device is adjusted to penetrate the skin of the patient promptly and easily for the patient. (e.g., refer to JP 2008-506468 W).

The applicator (sensor insertion device) disclosed in JP 2008-506468 W is provided with an insertion needle which is inserted together with a sensor, a plunger subassembly (movement mechanism) which moves the sensor and the insertion needle for sticking, and an attachment unit (implant member) which implants the sensor on the skin of a patient. An electrode unit (data process unit) which has a transmission function capable of transmitting the acquired information (biological information) of the detected blood glucose level to an external medical device is attached to the sensor.

In order to insert and implant a sensor inside the body of a patient using this type of sensor insertion device, the steps (usage procedure) listed below are generally performed.

Step [1]: Attaching a sensor to a sensor insertion device.
Step [2]: Detaching a safety mechanism of an insertion needle so as to be released to make the insertion needle movable.
Step [3]: Positioning the sensor insertion device at a desired position (insertion position) on the body of a subject and sticking an implant member onto the skin of the subject.
Step [4]: Operating the sensor insertion device to insert a detection element of the sensor and the insertion needle into the body of the subject.
Step [5]: Reracting the insertion needle from the sensor to implant the sensor and the implant member inside the body (and on the skin) of the subject.
Step [6]: Removing the sensor insertion device from the subject.
Step [7]: Connecting a data process unit to a part of the sensor exposed on the skin of the subject to leave the data process unit in place together with the sensor.

Among the above steps [1] to [7], in order to perform, in particular, steps [2], [5], and [6], it is necessary for an operator (mainly, a subject himself/herself) to perform complicated operations such as pressing a button and releasing a mating state between members of the sensor insertion device. Thus, it can be difficult for people unfamiliar with the insertion device (especially children and the elderly) to handle the sensor insertion device.

Further, as can be understood from the above, there are many operation steps. Thus, an operator may erroneously perform the sensor insertion operation, and, as a result, may fail to insert the sensor. This causes a burden to the subject.

Further, the safety mechanism detached in step [2] has to be discarded. This increases waste products, and therefore results in a lack of convenience.

SUMMARY OF INVENTION

One objective of certain embodiments of the present invention is to provide a sensor insertion device which easily inserts a sensor into the body of a subject.

Another objective of certain embodiments of the present invention is to provide a sensor insertion device capable of preventing an increase in the number of waste products.

Another objective of certain embodiments of the present invention is to provide a sensor insertion method capable of inserting a sensor into the body of a subject with a simple operation. An embodiment of the present invention provides a sensor insertion device for inserting a detection element of a sensor measuring biological information of a subject into the body of the subject. The sensor insertion device includes a device body to which a data process unit processing a signal including biological information detected by the detection element is attached, a movement mechanism detachably attached to the device body, the movement mechanism moving the detection element together with an insertion needle to be stuck into the body of the subject to insert the detection element and the insertion needle into the body of the subject, and a displacement preventing member to prevent displacement of the movement mechanism toward the body of the subject.

The movement mechanism includes a hollow guide member engageable with the device body, a needle holding member pushing the insertion needle to move inside the guide member, a grip member gripped by an operator, a pushing member held by the grip member and displaced to push the needle holding member interlocking with displacement of the grip member along the guide member caused by the operator, and a resilient member elastically biasing the needle holding member in a direction away from the device body.

The displacement preventing member blocks the grip member when the data process unit is not attached to the device body and, on the other hand, moves under a pushing action of the data process unit to release the blockage with respect to the grip member when the data process unit is attached to the device body. The insertion needle is stuck into the body of the subject when the pushing member is displaced along with displacement of the grip member released from the blockage by the displacement preventing member toward the body of the subject and the pushing member pushes the needle holding member. The pushing member remaining held by the grip member is engaged with the guide member when the pushing member reaches a displacement end point. The guide member is released from engagement with the device body by the grip member when the grip member and the pushing member reach the displacement end point. The needle holding member is displaced in a direction away from the device body by an action of the resilient member when the grip member and the pushing member reach the displacement end point, so that the detection element is implanted inside the body by the engagement between the pushing member and the guide member, the release of the engagement of the guide member with the device body, and the displacement of the needle holding member in the direction away from the device body.

In certain embodiments of the present invention, the safety mechanism is configured by blocking the grip member by the displacement preventing member. Further, the safety mechanism is released by a simple operation essential in the sensor insertion step of attaching the data process unit. This prevents an erroneous operation of inserting the insertion needle and the detection element into the body of a subject without attaching the data process unit thereto.

In addition, the above configuration enables the detection element to be inserted into the body and the movement mechanism to be detached from the device body merely by performing a simple operation of displacing the movement mechanism toward the body of the subject after releasing the safety mechanism. Thus, even a person unfamiliar with the sensor insertion device is not likely to perform an erroneous operation.

As described above, certain embodiments of the present invention make it possible to prevent an operator from erroneously performing the sensor insertion operation. Therefore, there is less burden on a subject.

In one aspect, the displacement preventing member includes a bar-like member attached to the guide member. In this case, in order to turn the bar-like member, the bar-like member may be directly pushed by the data process unit.

In one aspect, when the device body includes a base plate, a housing attached to the base plate, and a lid member attached to the housing to block an opening of the housing, the lid member may serve as the displacement preventing member. In this case, when the data process unit is attached to the device body, the data process unit pushes the base plate to displace the base plate. Along with this, the lid member turns to release the blockage with respect to the grip member. Accordingly, the safety mechanism is released.

In order to displace the needle holding member in a direction away from the device body under an action of the resilient member when the grip member and the pushing member reach the displacement end point, for example, the needle holding member may be provided as a long member and a slit may be formed along the longitudinal direction of the needle holding member. Further, a stopper is disposed on the slit, and an entrance portion which enters the notch is formed on the pushing member. In such a configuration, when the entrance portion climbs over the stopper and enters the slit, the needle holding member is displaced in the direction away from the device body under an action of the resilient member.

In order to release the guide member from the engagement with the device body when the grip member and the pushing member reach the displacement end point, an engagement portion of the guide member to be engaged with the device body may be formed on the tip of a spreading portion that spreads outward from the guide member.

In this case, the spreading portion is pushed by an inner wall of the grip member when the grip member is displaced toward the device body. As a result, the spreading portion is displaced in a direction approaching the guide member, that is, a direction away from the device body. Accordingly, the engagement of the engagement portion with the device body is released.

In one aspect, the resilient member may be held by a holding wall which is formed inside the guide member.

In one aspect, a catching portion which catches the sensor when the needle holding member reaches the displacement end point is formed on the device body. In this case, when the needle holding member returns to the direction away from the device body, the sensor is positioned and fixed by the catching portion. Thus, the detection element inserted into the body of the subject can be easily detached from the needle. That is, the catching portion serves as a retainer for the detection element.

In one aspect, a transmitter is attached to the device body as the data process unit. A transmitter is capable of performing wireless communication. Thus, it is possible to obtain biological information of a subject, for example, in an external medical device such as a display device and an electronic medical recording system.

Another embodiment of the present invention provides a sensor insertion method for inserting a detection element of a sensor measuring biological information of a subject into the body of the subject by a movement mechanism detachably attached to a device body holding a data process unit processing a signal including biological information detected by the detection element, wherein the movement mechanism includes a hollow guide member engageable with the device body, a needle holding member pushing the insertion needle to move inside the guide member, a grip member gripped by an operator, a pushing member held by the grip member and displaced to push the needle holding member interlocking with displacement of the grip member along the guide member caused by the operator, and a resilient member elastically biasing the needle holding member in a direction away from the device body.

The sensor insertion method includes the steps of disposing a displacement preventing member blocking the grip member to prevent displacement of the movement mechanism toward the body of the subject, allowing the device body to which the movement mechanism is attached by engagement of the guide member to come into contact with the subject, attaching the data process unit to the device body, moving the displacement preventing member under a pushing action of the data process unit to release blockage with respect to the grip member, displacing the pushing member to push the needle holding member interlocking with the grip member released from the blockage by the displacement preventing member to stick the insertion needle into the body of the subject and move the sensor, and moving the grip member, the pushing member, and the needle holding member to a displacement end point to engage the pushing member remaining held by the grip member with the guide member, to release the guide member from engagement with the device body by the grip member, and to displace the needle holding member in a direction away from the device body by an action of the resilient member so that the detection element is implanted inside the body.

Certain embodiments of the present invention make it possible to release the safety mechanism merely by performing an operation of attaching the data process unit to the device body. Further, an operator can insert the detection element of the sensor into the body of the subject and detach the movement mechanism from the device body merely by performing an operation of displacing the movement mechanism toward the body of the subject thereafter.

As can be understood from the above, the sensor insertion method includes a small number of steps. Thus, even a person unfamiliar with the sensor insertion device is not likely to perform an erroneous operation. Therefore, there is less burden on a subject.

In one aspect the displacement preventing member may be configured as a bar-like member attached to the guide member as described above. In this case, the bar-like member may be turned by directly pushing the bar-like member by the data process unit.

In one aspect, when the device body includes a base plate, a housing attached to the base plate, and a lid member attached to the housing to block an opening of the housing, the lid member may serve as the displacement preventing member. In this case, when the data process unit is attached to the device body, the base plate may be pushed by the data process unit to displace the base plate, and the lid member may be turned along with this.

In one aspect, in order to displace the needle holding member in the direction away from the device body under an action of the resilient member when the grip member and the pushing member reach the displacement end point, the needle holding member may be configured in the above manner and the entrance portion may be allowed to climb over the stopper and enter the slit.

In one aspect, in order to release the guide member from the engagement with the device body when the grip member and the pushing member reach the displacement end point, the guide member may be configured in the above manner, and the spreading portion may be pushed by the inner wall of the grip member displaced toward the device body to displace the engagement portion in the direction away from the device body.

In one aspect, a catching portion is disposed on the device body so that the sensor is caught by the catching portion when the needle holding member reaches the displacement end point. This is because of that, when the needle holding member returns to the direction away from the device body, detachment of the detection element is prevented by such a configuration.

BRIEF DESCRIPTION OF DRAWINGS

FIG. 26 is a vertical cross-sectional view of the sensor insertion device according to the second embodiment after the transmitter is attached to the device body.

DETAILED DESCRIPTION

Hereinafter, a sensor insertion method according to an embodiment of the present invention will be specifically described with reference to the accompanying drawings by showing preferred embodiments in relation with a sensor insertion device for performing the method.

Figure 1:
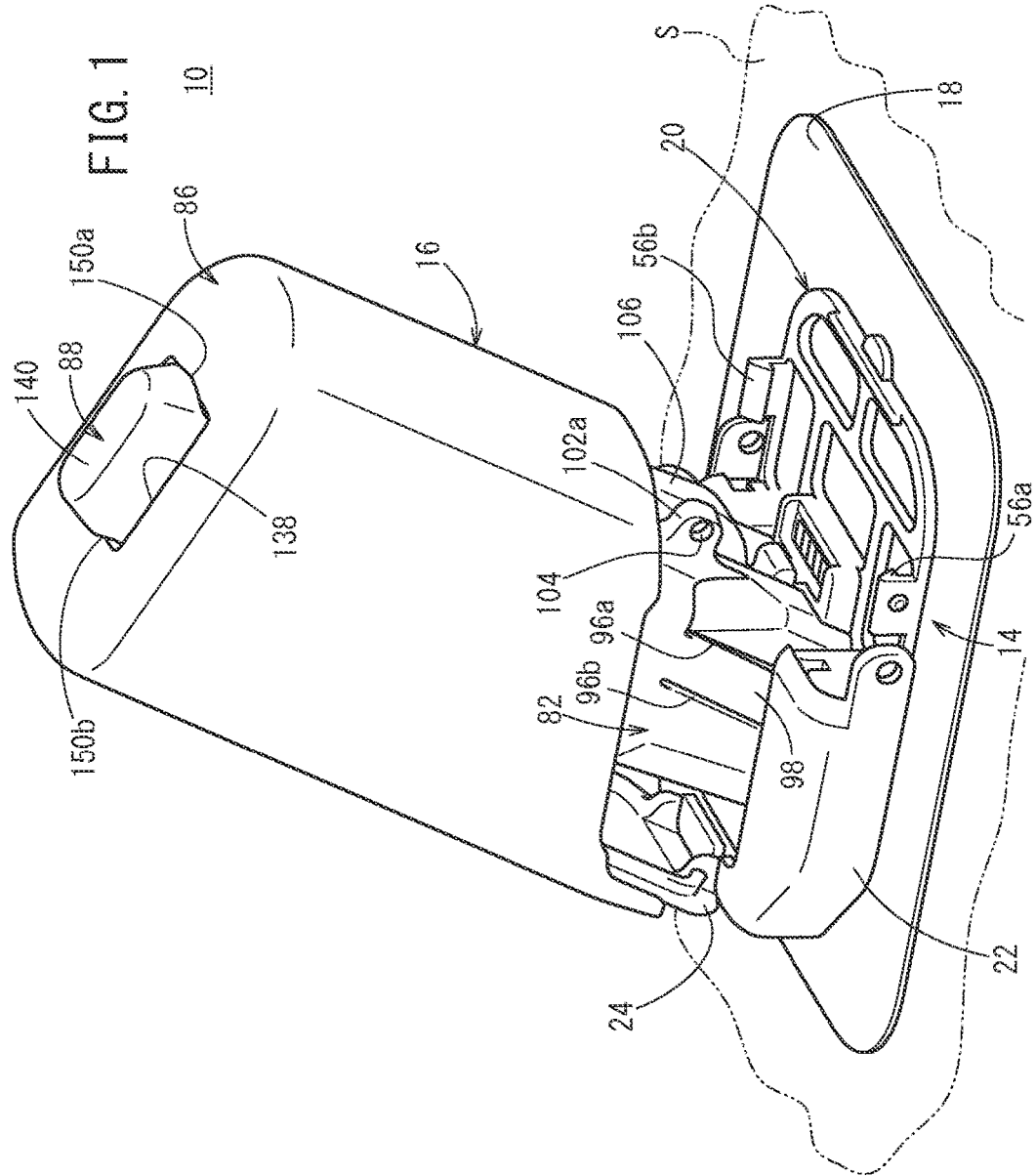
FIG. 1 is an overall schematic perspective view of a sensor insertion device according to a first embodiment of the present invention.
Figure 2:
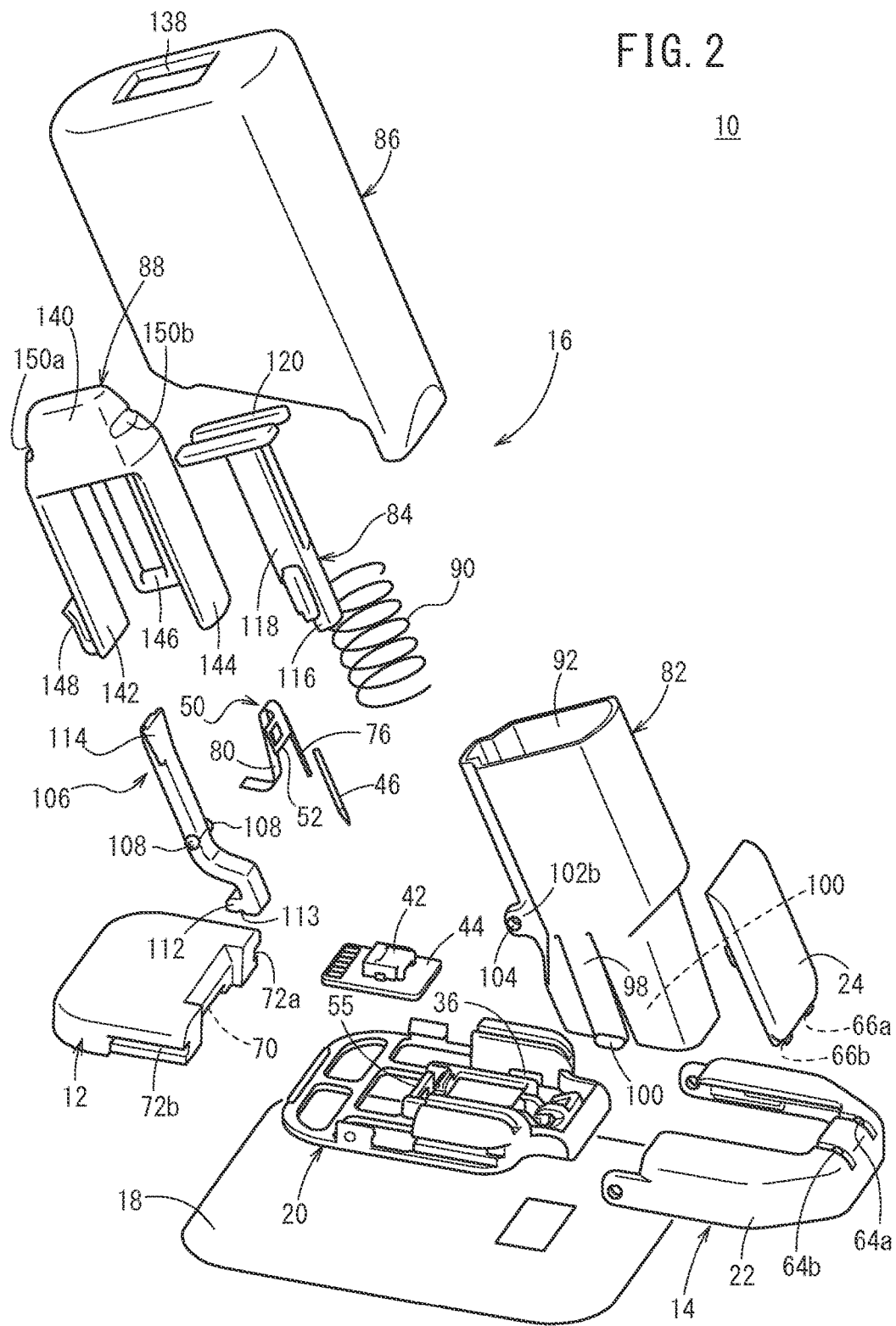
FIG. 2 is an exploded perspective view of the sensor insertion device.

FIG. 1 is an overall schematic perspective view of a sensor insertion device 10 according to a first embodiment. FIG. 2 is an exploded perspective view of the sensor insertion device 10. The sensor insertion device 10 is provided with a device body 14 to which a transmitter 12 (refer to FIG. 2) as a data process unit is attached and a movement mechanism 16. As illustrated in FIG. 1, the sensor insertion device 10 is placed at an appropriate position (e.g., an inconspicuous place with less body motion such as the abdomen) on the skin S of a patient (subject).

The sensor insertion device 10 is positioned on the skin S by an adhesive member 18 which is disposed on the bottom face of the device body 14. The lower end face of the adhesive member 18 is coated with an adhesive which has a sticking power sufficient to prevent the adhesive member 18 from easily peeling off when stuck to the skin S of the patient. Further, a part of the upper end face of the adhesive member 18, the part facing the device body 14, is also coated with an adhesive.

First, the device body 14 will be described. The device body 14 includes a base plate 20, a housing 22 which is attached to the base plate 20, and a lid member 24 which blocks an opening of the housing 22 (refer to FIG. 2).

Figure 3:
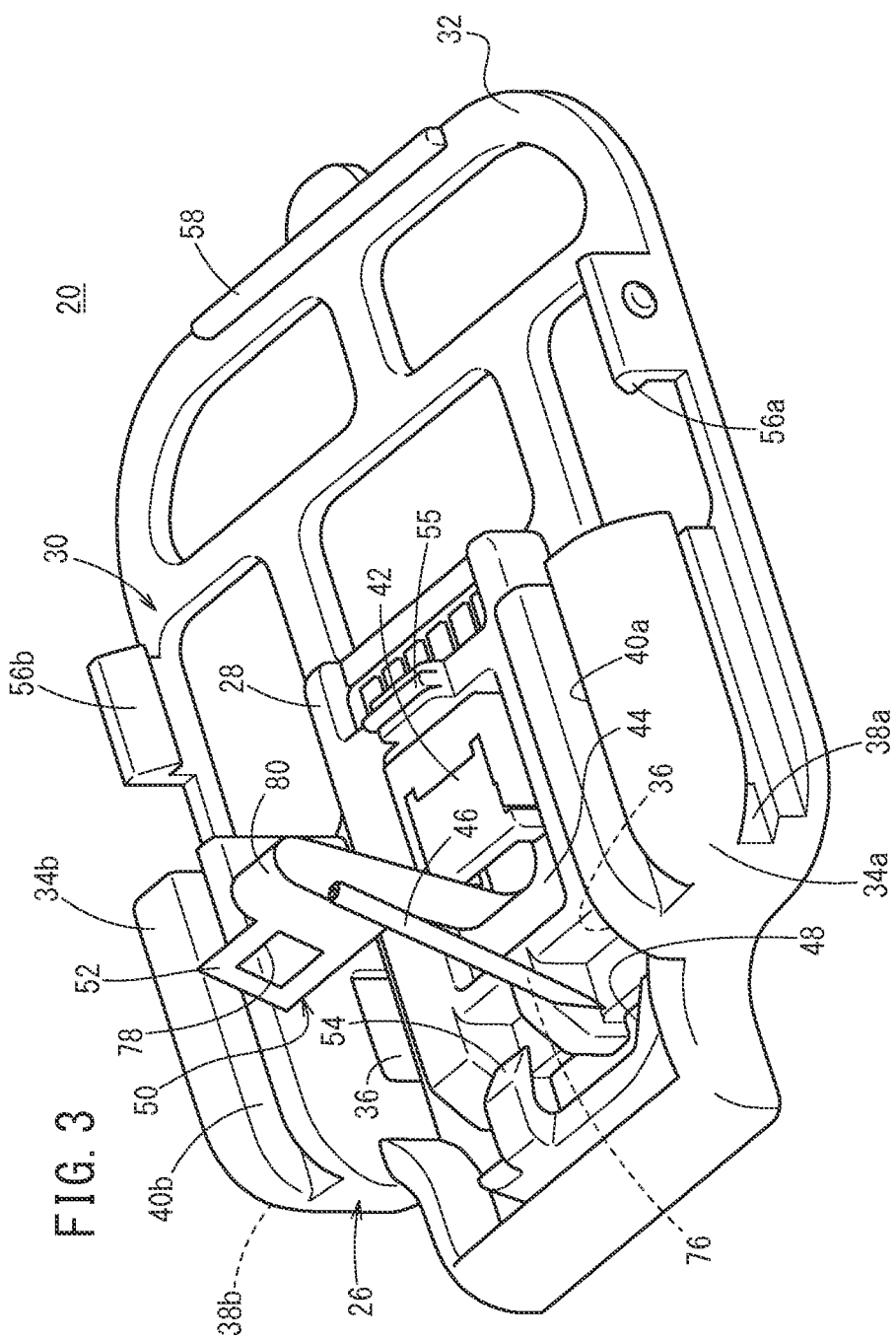
FIG. 3 is a schematic perspective view of a base plate of a device body illustrated in relation with the position of a sensor.

As illustrated in FIG. 3, the base plate 20 includes a first attachment portion 26, a circuit board holding portion 28, and a second attachment portion 30. The first attachment portion 26 includes two thick standing portions 34a and 34b each of which stands on a bottom frame 32. Engagement recesses 36 are formed in a depressed form near bottoms of opposed vertical walls of the standing portions 34a and 34b. A first insertion groove 38a and a second insertion groove 40a are respectively formed on the outer side face and the top face of the standing portion 34a along the longitudinal direction of the base plate 20. A first insertion groove 38b and a second insertion groove 40b are respectively formed on the outer side face and the top face of the standing portion 34b along the longitudinal direction of the base plate 20.

The circuit board holding portion 28 is arranged between the standing portions 34a and 34b, and holds a circuit board 44 which is provided with a connector 42.

In the base plate 20, an insertion opening 48 for inserting an insertion needle 46 (described below) therethrough is formed on the tip of the circuit board holding portion 28. Further, a catching claw 54 (catching portion) for catching a sensor base 52 of a sensor 50 is formed above the insertion opening 48. Further, a lock portion 55 for preventing displacement of a safety bar 106 (described below, refer to FIG. 1) when the transmitter 12 is not attached to the base plate 20 is formed on the rear end of the circuit board holding portion 28.

The second attachment portion 30 is a region for attaching the transmitter 12 (refer to FIG. 6) thereto. Grasping claws 56a and 56b which project vertically upward are formed on the second attachment portion 30. A blocking portion 58 which is formed of a generally semicylindrical body lying on the side is disposed on the end of the second attachment portion 30.

Figure 4:
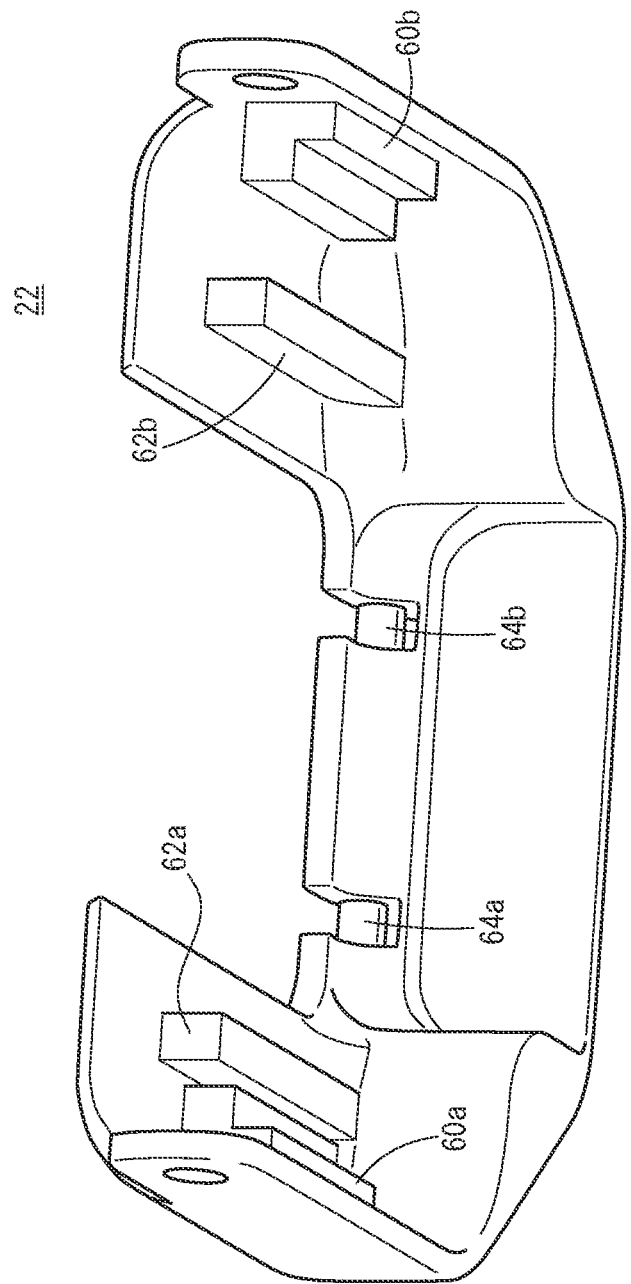
FIG. 4 is a schematic perspective view of a housing of the device body viewed from the lower side.

The housing 22 has a generally U shape. As illustrated in FIG. 4, the housing 22 includes first prisms 60a and 60b which project along the horizontal direction are formed on the inner side of side walls and second prisms 62a and 62b which project downward along the vertical direction are formed on a ceiling wall. The first prisms 60a and 60b are slidably inserted into the first insertion grooves 38a and 38b, respectively. The second prisms 62a and 62b are slidably inserted into the second insertion grooves 40a and 40b, respectively.

Generally cylindrical locking shafts 64a and 64b for locking the lid member 24 are disposed on the tip of the housing 22.

Figure 5:
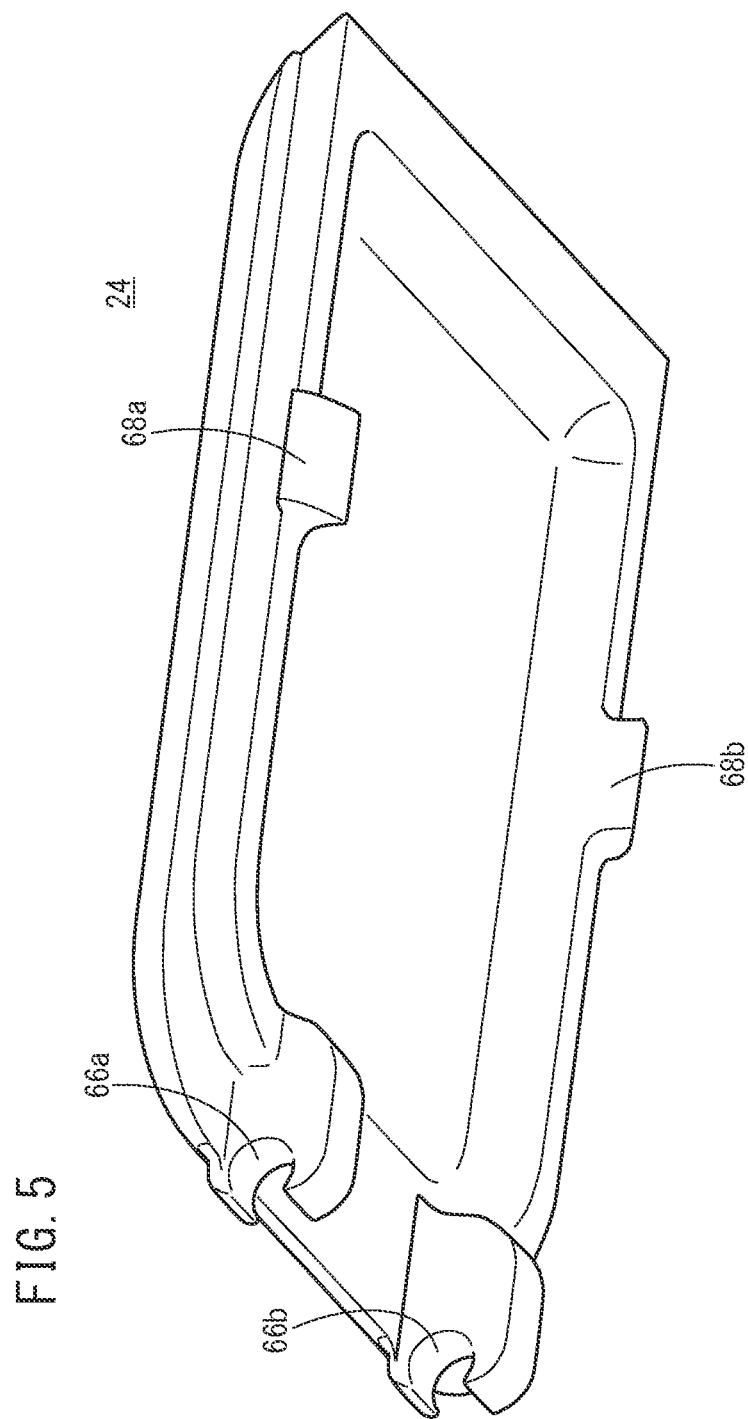
FIG. 5 is a schematic perspective view of a lid member of the device body viewed from the lower side.

On the other hand, as illustrated in FIG. 5, circular arc-like recesses 66a and 66b are formed on the tip of the lid member 24. The locking shafts 64a and 64b are respectively inserted into the circular arc-like recesses 66a and 66b. The lid member 24 is tiltably locked to the housing 22 by inserting the locking shafts 64a and 64b respectively into the circular arc-like recesses 66a and 66b.

Hooking claws 68a and 68b which project vertically downward are formed on the lower end face of the lid member 24. These hooking claws 68a and 68b are hooked on the ceiling wall of the housing 22 when the lid member 24 is in a closed state.

Figure 6:
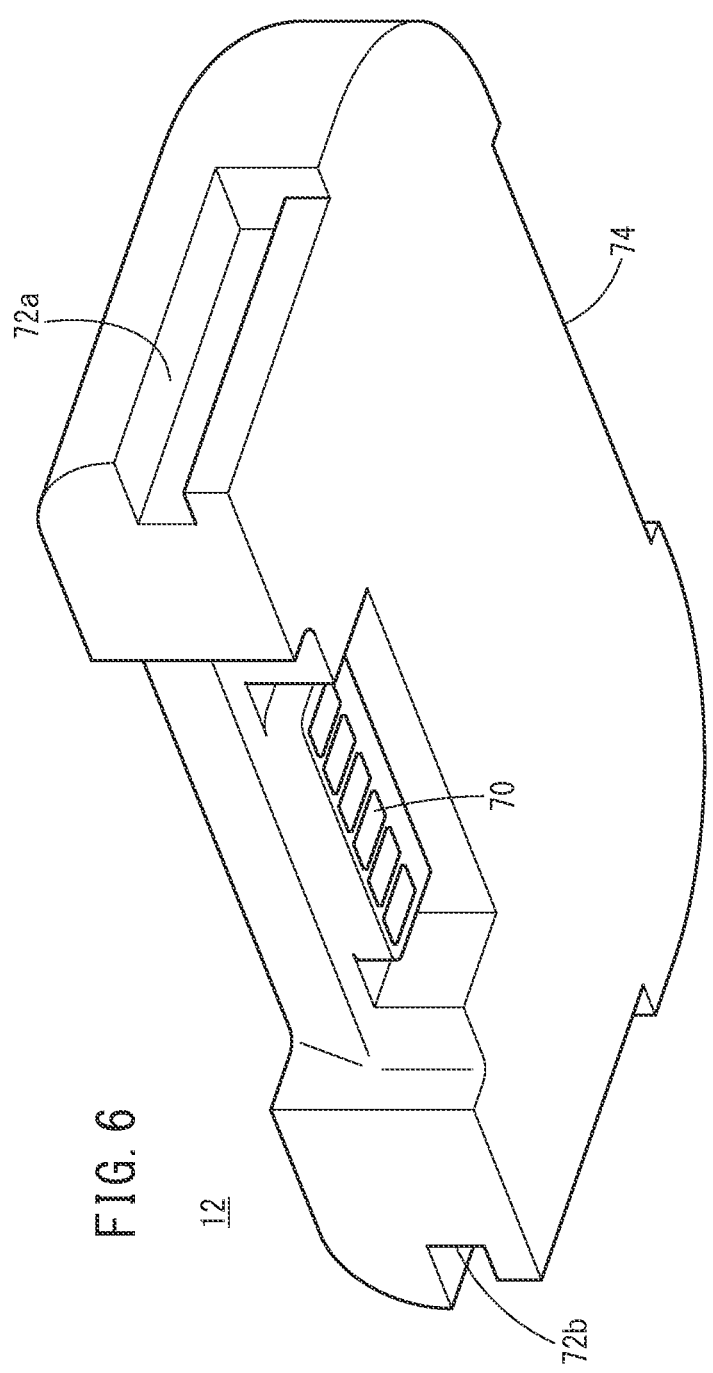
FIG. 6 is a schematic perspective view of a transmitter to be attached to the device body from the lower side.

The transmitter 12 attached to the second attachment portion 30 is electrically connected to the circuit board 44 through an electrode 70 illustrated in FIG. 6 and used for receiving a signal, converting the signal into information, and wirelessly transmitting the information to an external medical device (e.g., a display device or an electronic medical recording system, not illustrated) automatically or by an operation. Accordingly, it is possible to manage the blood glucose level or the like of a subject (patient) in a place away from the subject.

Grooves 72a and 72b to be grasped are formed in a depressed form on opposite side parts of the transmitter 12. The grasping claws 56a and 56b (refer to FIG. 3) are respectively inserted into the grooves 72a and 72b. Further, an entrance recess 74 is formed on the bottom of one end of the transmitter 12. The blocking portion 58 enters the entrance recess 74.

As will be described below, the transmitter 12 is attached to the device body 14 before a detection element 76 (refer to FIG. 2) of the sensor 50 is inserted into the body of a subject by the sensor insertion device 10.

The movement mechanism 16 is used for moving the detection element 76 illustrated in FIG. 2 together with the insertion needle 46 so as to be inserted into the body of a subject.

Figure 7:
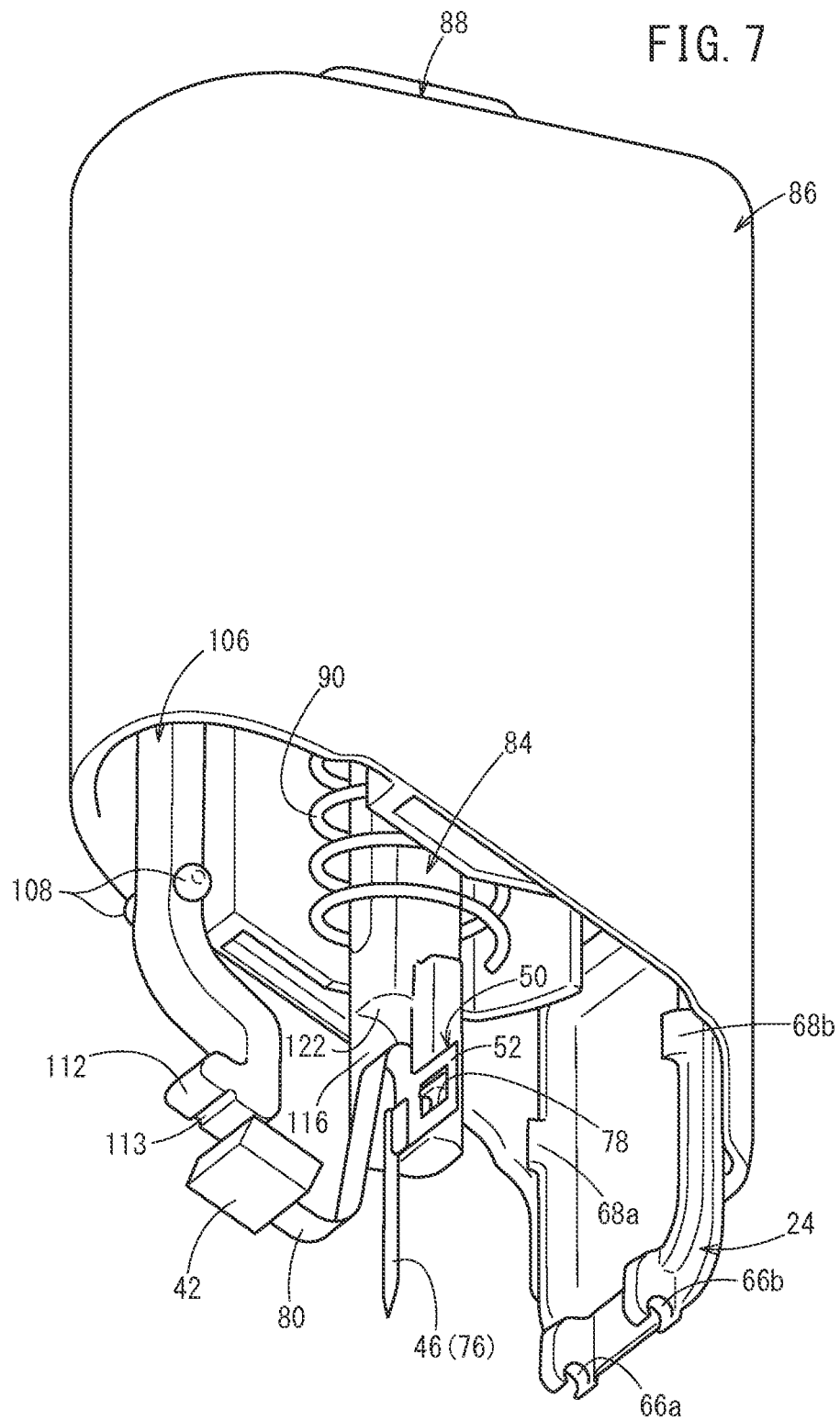
FIG. 7 is a principal part schematic perspective view illustrating the positional relationship between a grip member, the lid member, a needle holder (needle holding member), a safety bar, and the sensor.

First, the sensor 50 will be described. The sensor 50 includes the detection element 76 and the sensor base 52. The detection element 76 is formed in a long shape and housed inside the insertion needle 46 as illustrated in FIGS. 3 and 7. The detection element 76 detects, for example, information about the concentration of glucose contained in a body fluid component of a patient (biological information: blood glucose level).

On the other hand, the sensor base 52 is formed in a thin plate shape and coupled to the base end of the detection element 76. The sensor base 52 has a rectangular hole 78 to be caught which is formed to penetrate the sensor base 52. The tip of the catching claw 54 passes through the hole 78.

The sensor base 52 is coated with an insulation material, and has a sensor circuit (not illustrated) disposed inside thereof. As the sensor circuit using fluorescent dye, for example, a structure in which a base body made of, for example, silicon, a light receiving element, a protective film, a filter, a light emitting element, an indicator layer, and the like are laminated is employed.

A flexible cable 80 for electrically connecting the detection element 76 and the transmitter 12 is disposed on the sensor base 52. Information about, for example, the glucose concentration detected by the detection element 76 is transmitted to the transmitter 12 through the flexible cable 80 and the connector 42.

Next, the insertion needle 46 will be described. The insertion needle 46 is made of a metal material (e.g., stainless steel) having rigidity so as to be easily stuck into the skin S of a patient. Further, a part of the tip of the insertion needle 46 is cut to have an acute angle (sharpness) to allow the insertion needle 46 to be easily stuck into the skin S.

The cross section in the horizontal direction of the insertion needle 46 is formed in a generally C shape (or a generally U shape), and a hollow groove is defined inside the C-shaped cross section. The hollow groove extends along the longitudinal direction of the insertion needle 46, and is capable of housing the detection element 76 of the sensor 50 therein. That is, the detection element 76 is covered with the insertion needle 46.

Next, the movement mechanism 16 for moving the detection element 76 and the insertion needle 46 configured in the above manner toward a subject will be described.

As illustrated in FIG. 2, the movement mechanism 16 includes a guide member 82 which is engageable with the device body 14, a needle holder 84 (needle holding member) which pushes the insertion needle 46 to move, a grip member 86 which is gripped by an operator, a pusher 88 (pushing member) which pushes the needle holder 84, and a coil spring 90 (resilient member) which elastically biases the needle holder 84.

Figure 8:
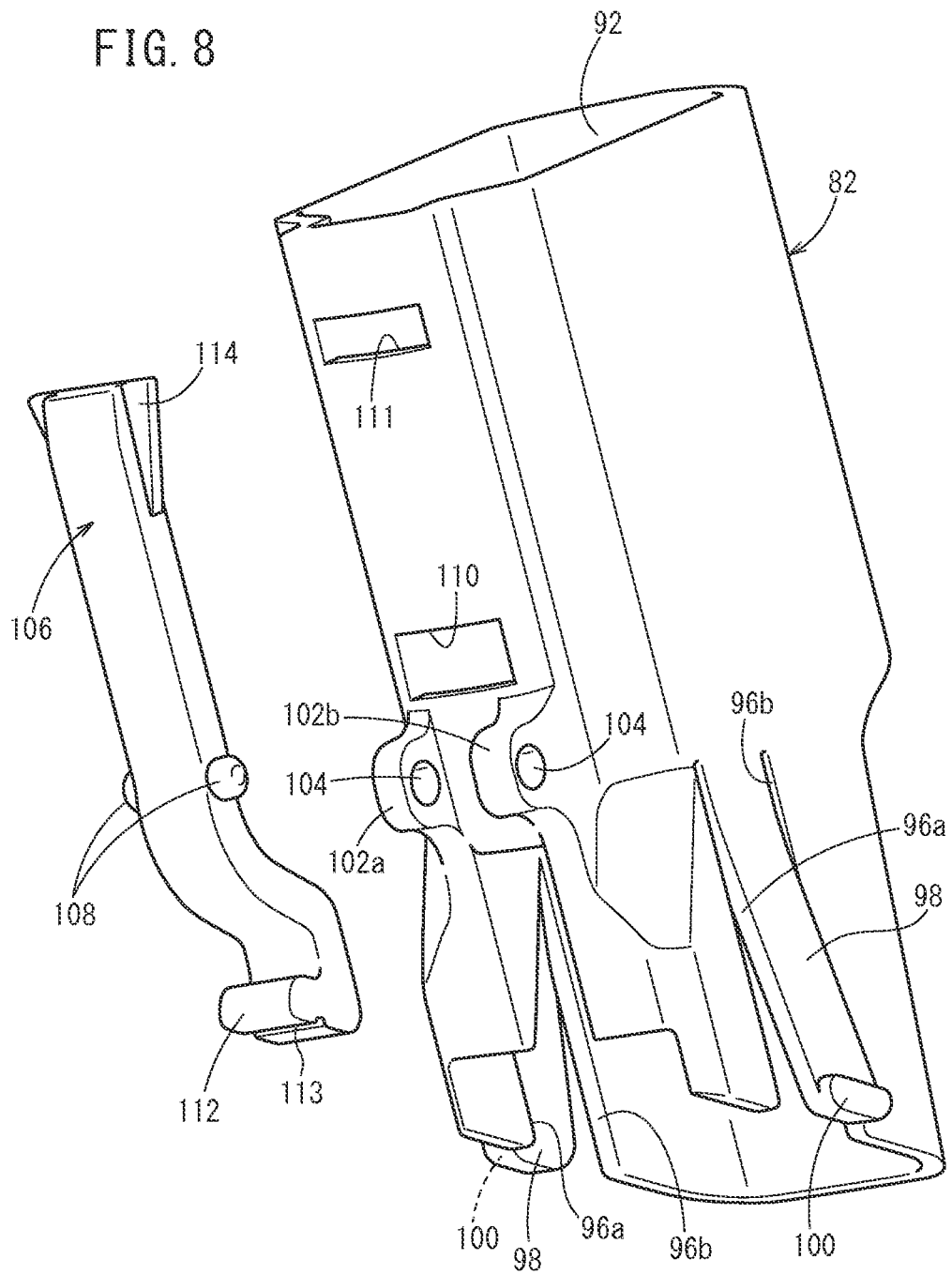
FIG. 8 is a schematic perspective view of a guide member with the safety bar.
Figure 9:
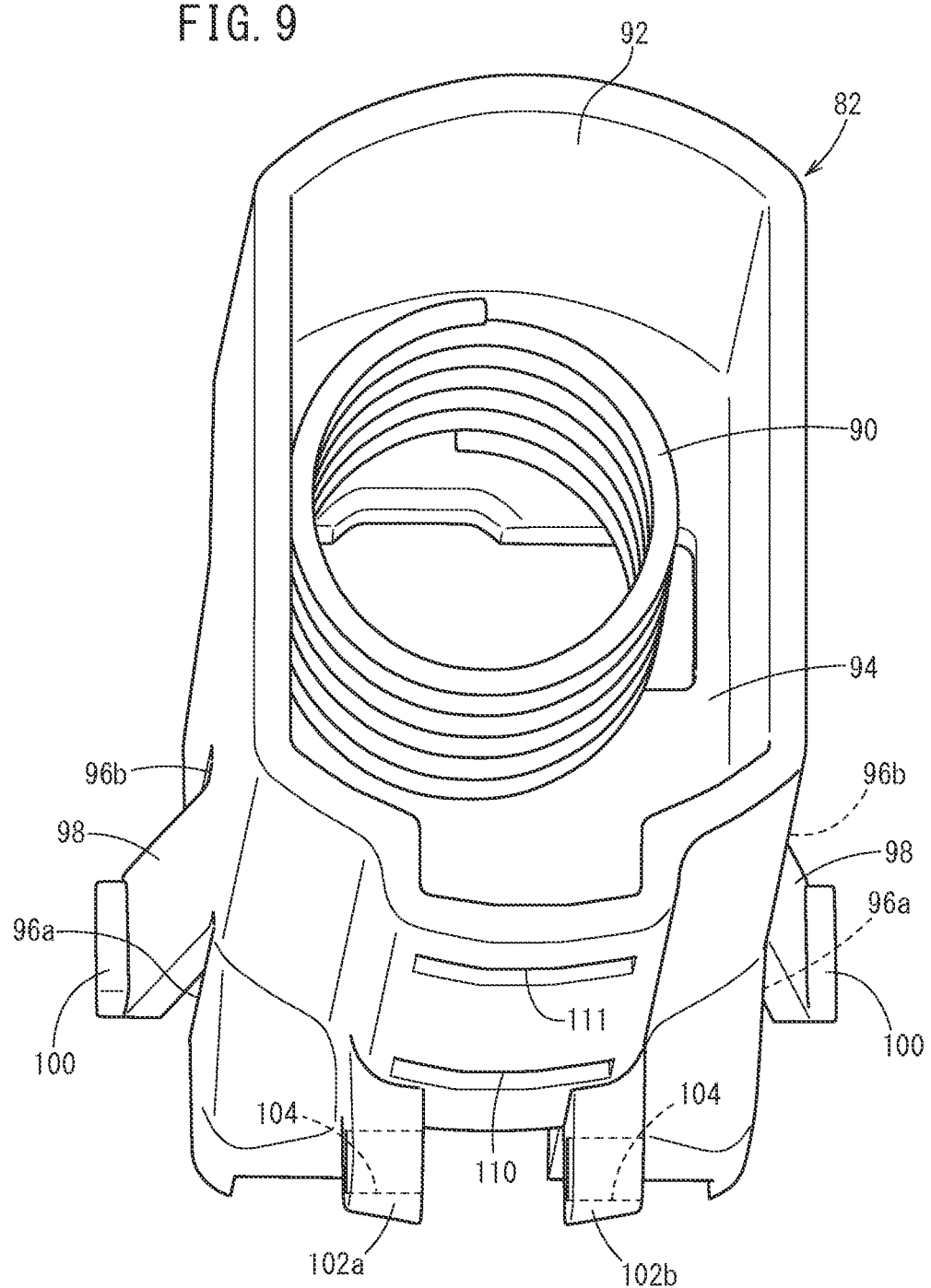
FIG. 9 is a schematic perspective view of the guide member viewed from the upper side.

As illustrated in FIGS. 8 and 9, the guide member 82 is provided as a hollow body which is slightly inclined relative to the vertical direction. That is, an insertion hole 92 is formed on the guide member 82 along the longitudinal direction thereof.

A holding wall 94 is formed inside the guide member 82 in a manner to narrow the insertion hole 92 (refer to FIG. 9). The lower end of the coil spring 90 is seated on the holding wall 94. In other words, the coil spring 90 is held by the holding wall 94.

Two notched grooves 96*a* and 96*b* are formed on each side wall on the long side of the guide member 82 (refer to FIG. 8). A part between the notched grooves 96*a* and 96*b* spreads outward from the guide member 82. Hereinafter, the part between the notched grooves 96*a* and 96*b* is referred to as a spreading portion 98.

An engagement projection 100 is formed on the tip of each spreading portion 98. These engagement projections 100 are engaged with the respective engagement recesses 36 (refer to FIG. 3) formed on the base plate 20 of the device body 14.

Further, two shaft support portions 102*a* and 102*b* are formed in a projecting form on one side wall on the short side of the guide member 82. A turning shaft 108 of a safety bar 106 (bar-like member) as a displacement preventing member is turnably supported on support holes 104 of the shaft support portions 102*a* and 102*b*. On the same side wall as above, a first locking window 110 and a second locking window 111 are formed in a penetrating manner in this order from the lower side.

The safety bar 106 is formed as a long member, and has a portion 112 to be pushed which is formed in a projecting form on a lower end thereof and extends in a direction perpendicular to the longitudinal direction. A locking recess 113 to be engaged with the lock portion 55 (refer to FIG. 3) is formed on the lower end face of the portion 112 and depressed upward. The turning shaft 108 to be inserted into the support holes 104 of the shaft support portions 102*a* and 102*b* is formed on the middle part in the longitudinal direction of the safety bar 106 and projects along the width direction thereof. A wide portion 114 which spreads in the width direction is formed on an upper end of the safety bar 106.

Figure 10:
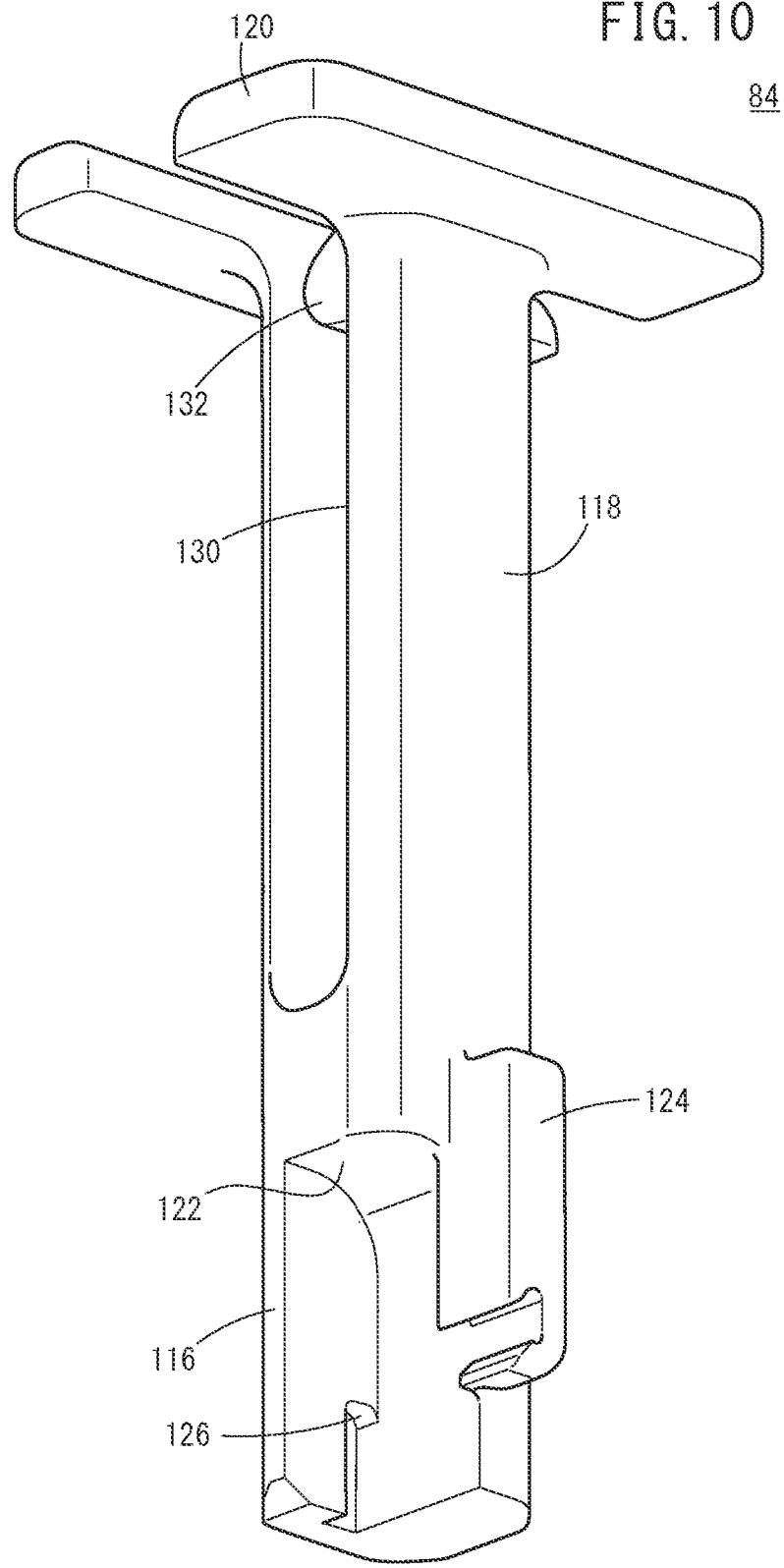
FIG. 10 is an overall schematic perspective view of the needle holder (needle holding member).

The needle holder 84 is inserted into the insertion hole 92 of the guide member 82. As illustrated in FIG. 10, the needle holder 84 includes a needle holding portion 116 which holds the insertion needle 46, a long body 118, and a wide head 120 which are formed in this order from the lower side toward the upper side.

Figure 11:
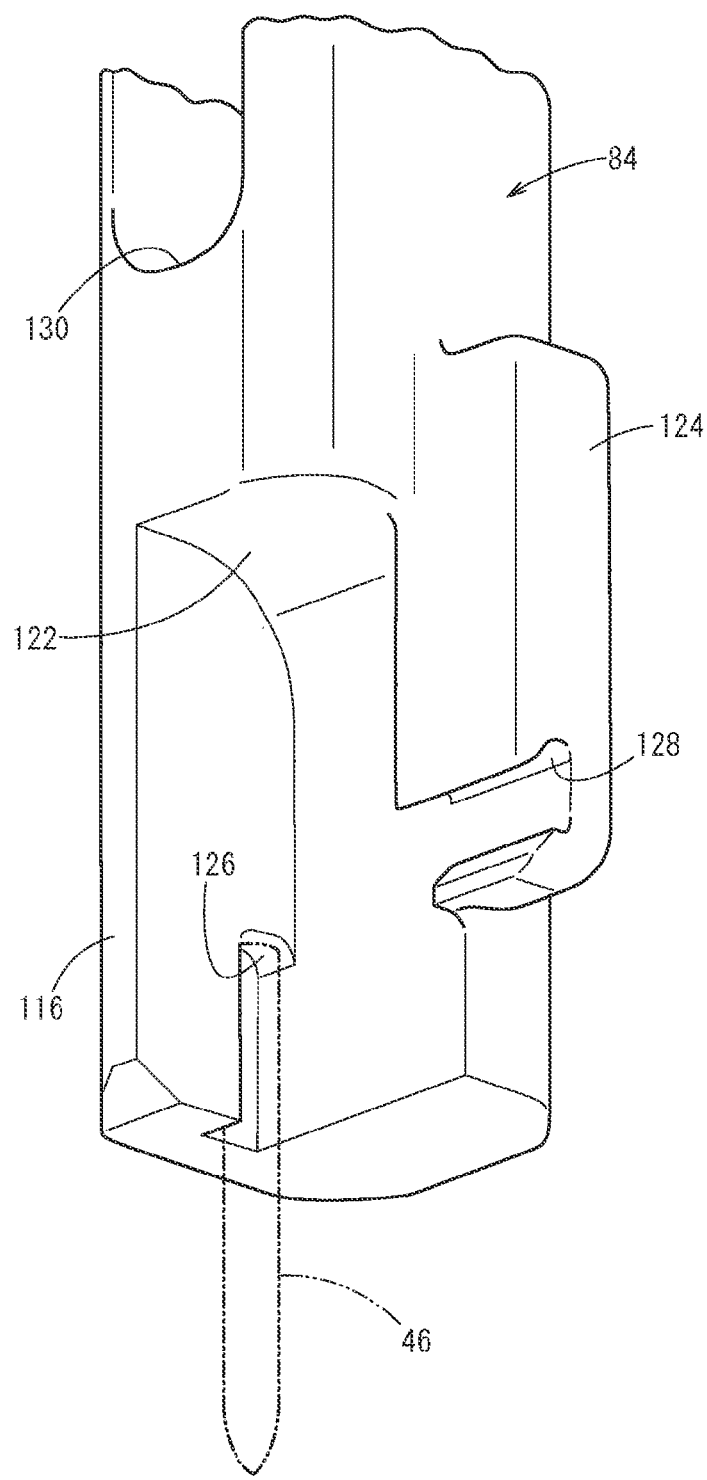
FIG. 11 is a principal part enlarged perspective view of the needle holder.

As illustrated in FIG. 11, the needle holding portion 116 has a notched portion 122 which is formed by notching a part of the needle holding portion 116 by approximately 90° and a base holding portion 124 which is formed in a projecting form adjacent to the notched portion 122. A needle step portion 126 is formed on the notched portion 122, and the insertion needle 46 is disposed on the needle step portion 126. On the other hand, a base step portion 128 is formed on the base holding portion 124 (refer to FIGS. 7 and 11), and the sensor base 52 comes into contact with the base step portion 128. The formation of the notched portion 122 prevents the flexible cable 80 from interfering with the needle holding portion 116.

As illustrated in FIG. 10, the needle holder 84 includes a slit 130 which is formed from the head 120 through the body 118. The needle holder 84 also includes a stopper 132 which is disposed on the slit 130 at a position near the head 120. The stopper 132 bulges in a direction substantially perpendicular to the longitudinal direction of the slit 130.

Figure 12:
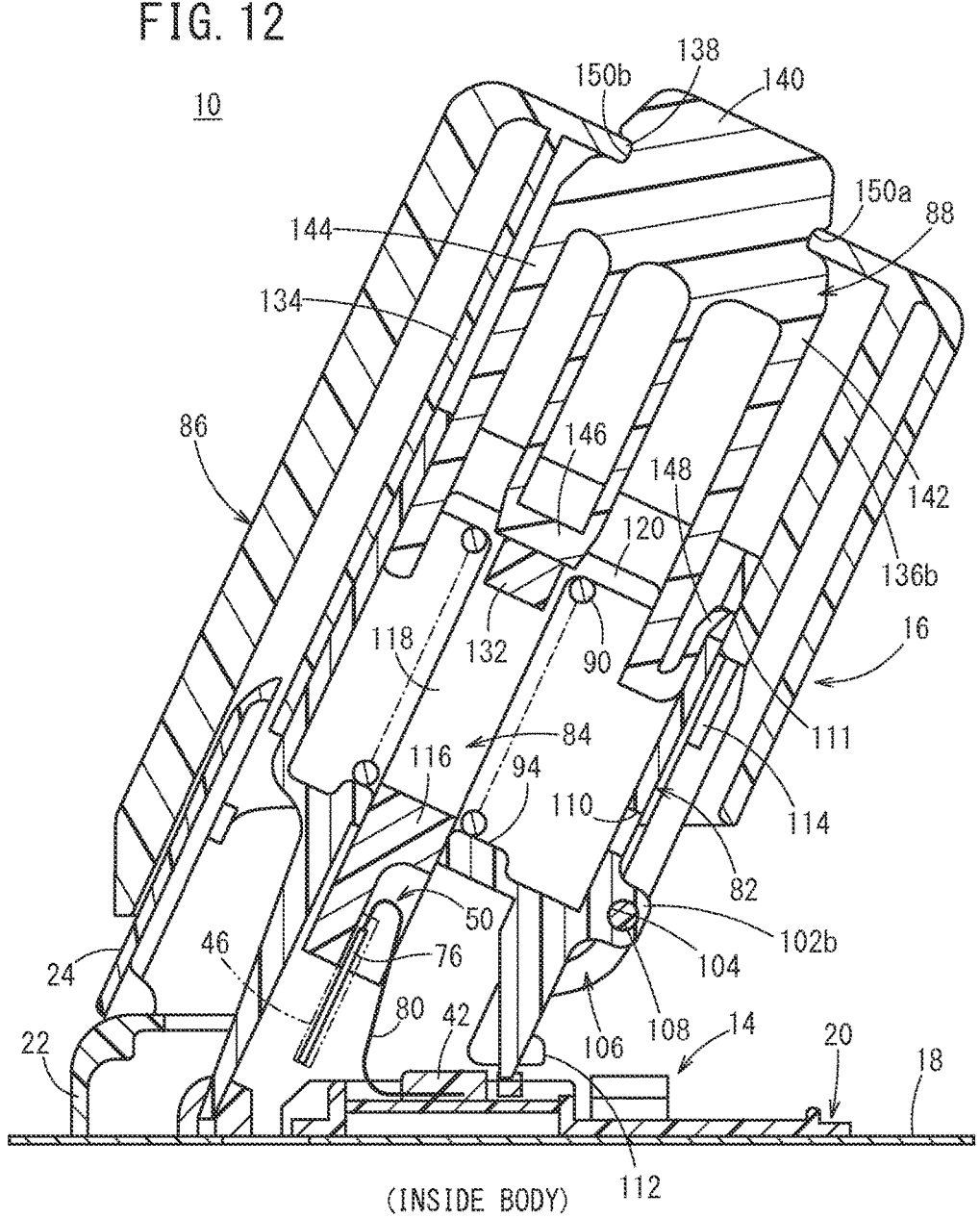
FIG. 12 is a vertical cross-sectional view of the sensor insertion device before a movement mechanism is displaced.

As can be understood from FIGS. 7 and 12, the body 118 of the needle holder 84 is inserted into the coil spring 90. An upper end of the coil spring 90 is seated on the lower end face of the head 120. That is, the coil spring 90 is located between the holding wall 94 of the guide member 82 and the head 120 of the needle holder 84.

As illustrated in FIGS. 1 and 2, the grip member 86 is provided as a hollow member which is inclined corresponding to the guide member 82.

Figure 13:
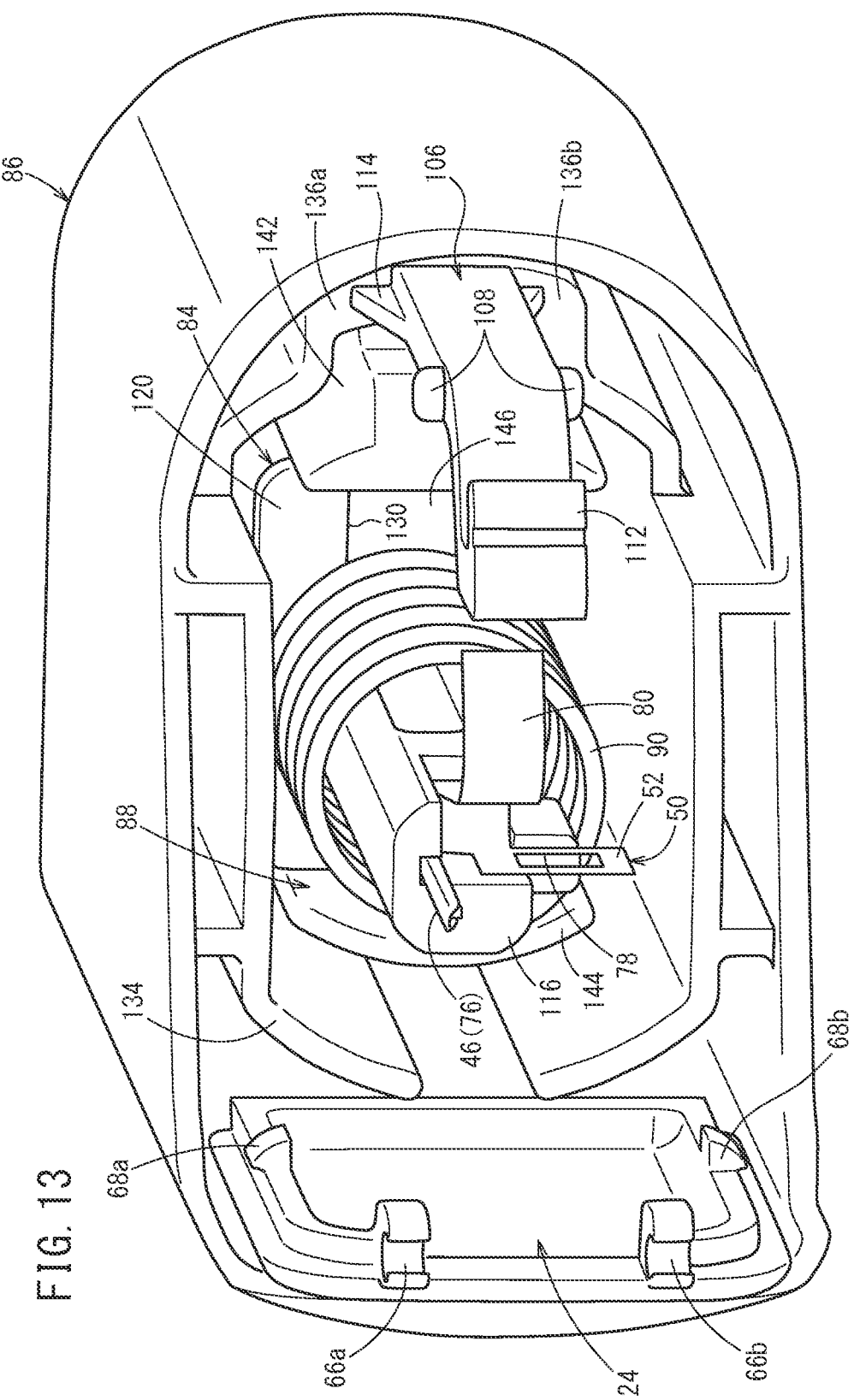
FIG. 13 is a lower-side plan view illustrating the positional relationship between the grip member, the lid member, the needle holder, a coil spring (resilient member), the safety bar, and the sensor.

As illustrated in FIG. 13, a surrounding wall 134 for surrounding and thereby holding the guide member 82 is formed inside the grip member 86. Further, two holding pillars 136*a* and 136*b* which extend along the longitudinal direction of the grip member 86 are formed near a short inclined surface. A clearance between the holding pillars 136*a* and 136*b* is set smaller than the dimension in the width direction of the wide portion 114 of the safety bar 106. Thus, the safety bar 106 is blocked by the holding pillars 136*a* and 136*b*.

An engagement hole 138 (refer to FIGS. 1 and 2) is formed in a penetrating manner on a flat upper end face of the grip member 86.

Figure 14:
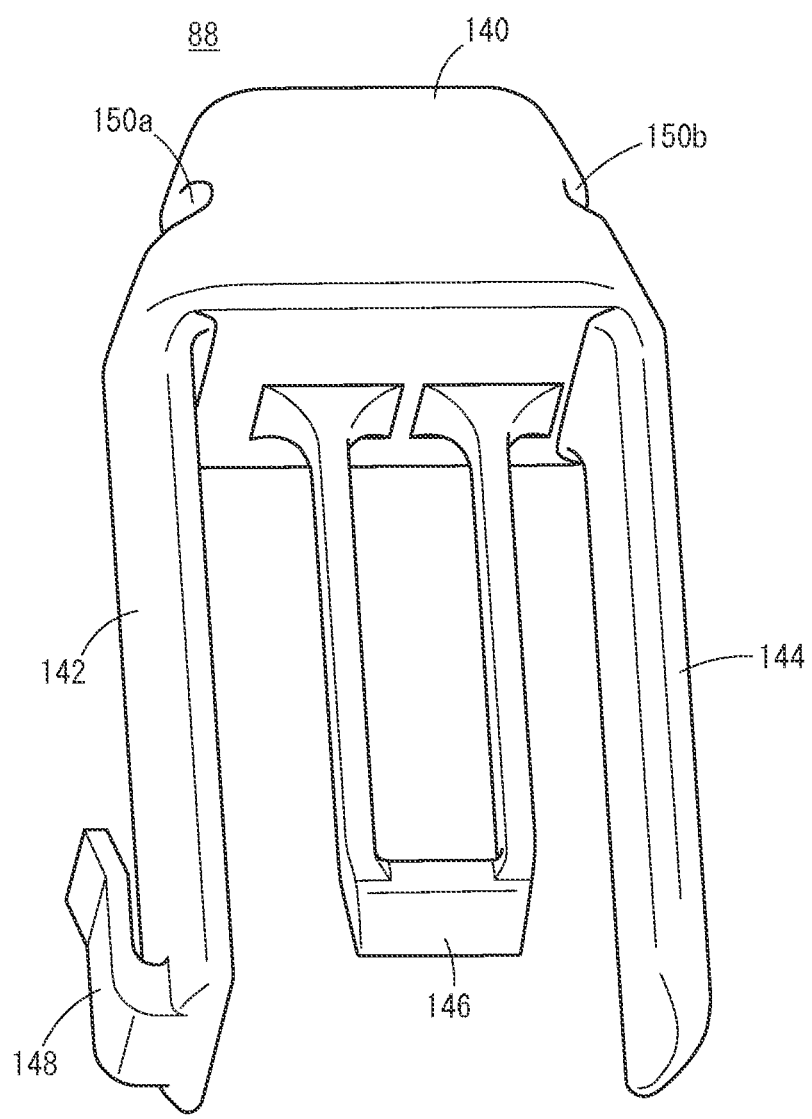
FIG. 14 is an overall schematic perspective view of a pusher (pushing member).

As illustrated in FIG. 14, the pusher 88 includes a head 140 which has a quadrangular pyramid shape without one top, a first hanging portion 142 and a second hanging portion 144 which hang down from two long sides of the bottom face of the head 140, and an entrance portion 146 which is disposed between the first hanging portion 142 and the second hanging portion 144 and extends in the same direction as the extending direction of the first hanging portion 142 and the second hanging portion 144. The first hanging portion 142 and the second hanging portion 144 are arranged at opposed positions. The head 120 of the needle holder 84 is slidably supported between the first hanging portion 142 and the second hanging portion 144.

The tip of the first hanging portion 142 is folded back to extend outward from the first hanging portion 142 to form a folded portion 148. As will be described below, the folded portion 148 is locked on the second locking window 111 of the guide member 82. On the other hand, the second hanging portion 144 which extends along the insertion hole 92 is held by the insertion hole 92.

The entrance portion 146 faces the slit 130 of the needle holder 84. The tip of the entrance portion 146 abuts on the stopper 132. That is, the entrance portion 146 pushes the stopper 132 to thereby push the needle holder 84. When the needle holder 84 is displaced by the pushing and reaches a displacement end point, the entrance portion 146 climbs over the stopper 132 and enters the slit 130.

Engagement grooves 150*a* and 150*b* are formed on the respective two side faces on the short sides of the bottom face of the head 140. As illustrated in FIGS. 1, 12, and the like, a part of the head 140 passes through the engagement hole 138 from the inside of the grip member 86 so as to be exposed from the engagement hole 138.

When the head 140 passes through the engagement hole 138, the engagement hole 138 of the grip member 86 is elastically deformed to expand. Then, when the positions of the engagement grooves 150a and 150b are aligned with the engagement hole 138, the engagement hole 138 is contracted to return to its original shape. It is needless to say that the inner wall of the engagement hole 138 enters the engagement grooves 150a and 150b. Accordingly, the pusher 88 and the grip member 86 are engaged with each other.

The sensor insertion device 10 according to the first embodiment is basically configured in the above manner. Next, effects of the sensor insertion device 10 will be described in relation with an operation thereof (sensor insertion method).

First, the lock portion 55 (refer to FIG. 3) of the base plate 20 is engaged with the locking recess 113 which is formed on the lower end face of the portion 112 to be pushed of the safety bar 106. Then, the transmitter 12 is attached to the device body 14 in which the displacement of the safety bar 106 is prevented by the engagement between the lock portion 55 and the locking recess 113. That is, the grasping claws 56a and 56b are respectively inserted into the grooves 72a and 72b which are formed on the opposite side parts of the transmitter 12. In this state, the transmitter 12 is allowed to slide toward the first attachment portion 26. The slide finishes when the tip face of the transmitter 12 comes into contact with the rear end face of the housing 22 and the blocking portion 58 enters the entrance recess 74. That is, the transmitter 12 is attached to the second attachment portion 30 of the base plate 20.

Figure 15:
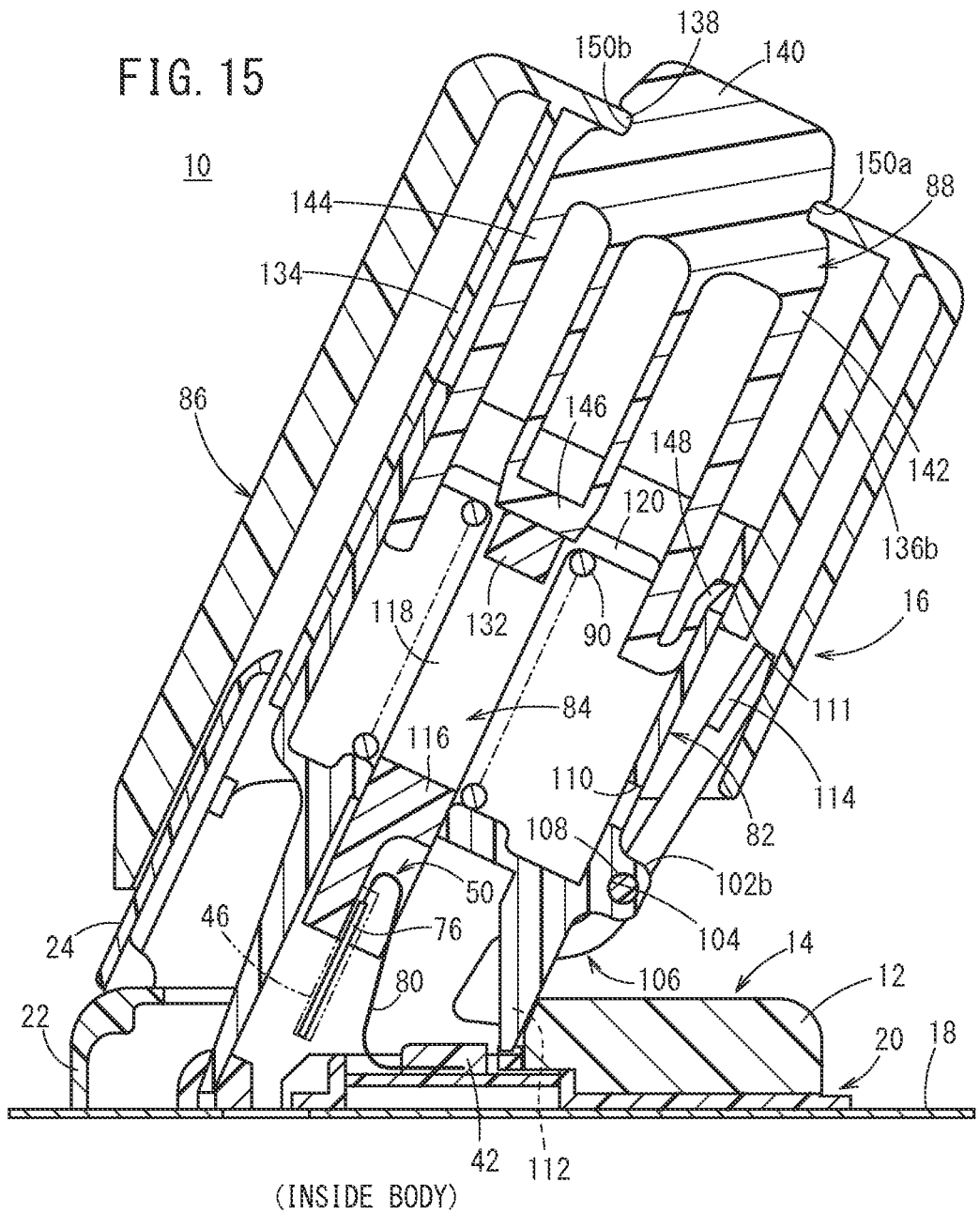
FIG. 15 is a vertical cross-sectional view of the sensor insertion device illustrating a state in which lock of the safety bar is released along with attachment of the transmitter to the device body.

When the transmitter 12 is attached to the second attachment portion 30 in this manner, as illustrated in FIG. 15, the portion 112 of the safety bar 106 is pushed by the tip face of the transmitter 12. As a result, the locking recess 113 formed on the lower end face of the portion 112 is disengaged from the lock portion 55 (both refer to FIG. 2). Accordingly, the safety bar 106 is released from the lockup by the base plate 20 (device body 14). Thus, the safety bar 106 turns around the turning shaft 108. Along with this, the wide portion 114 of the safety bar 106 is disengaged from the holding pillars 136a and 136b of the grip member 86.

When the upper end face of the wide portion 114 of the safety bar 106 abuts on the lower end faces of the holding pillars 136a and 136b, the holding pillars 136a and 136b are blocked by the wide portion 114. Thus, it is not possible to displace the grip member 86. In other words, when the transmitter 12 is not attached, it is not possible to move the insertion needle 46 and the detection element 76. Therefore, it is possible to prevent an erroneous operation of inserting the insertion needle 46 and the detection element 76 into the body without attaching the transmitter 12 thereto.

At this point, the lid member 24 is supported between the inner wall of the grip member 86 and the surrounding wall 134 and housed inside the grip member 86. It is needless to say that the locking shafts 64a and 64b (refer to FIG. 4) formed on the housing 22 are previously respectively inserted into the circular arc-like recesses 66a and 66b (refer to FIG. 5) of the lid member 24.

The folded portion 148 of the pusher 88 is locked on the second locking window 111 formed near the upper end of the guide member 82. This prevents the grip member 86 and the pusher 88 from moving away from the device body 14 and coming off the guide member 82.

Then, a release paper stuck on the lower end face of the adhesive member 18 is peeled off, and the adhesive member 18 is stuck at an appropriate position on the skin S of a patient. Accordingly, the sensor insertion device 10 is positioned on the skin S.

Figure 16:
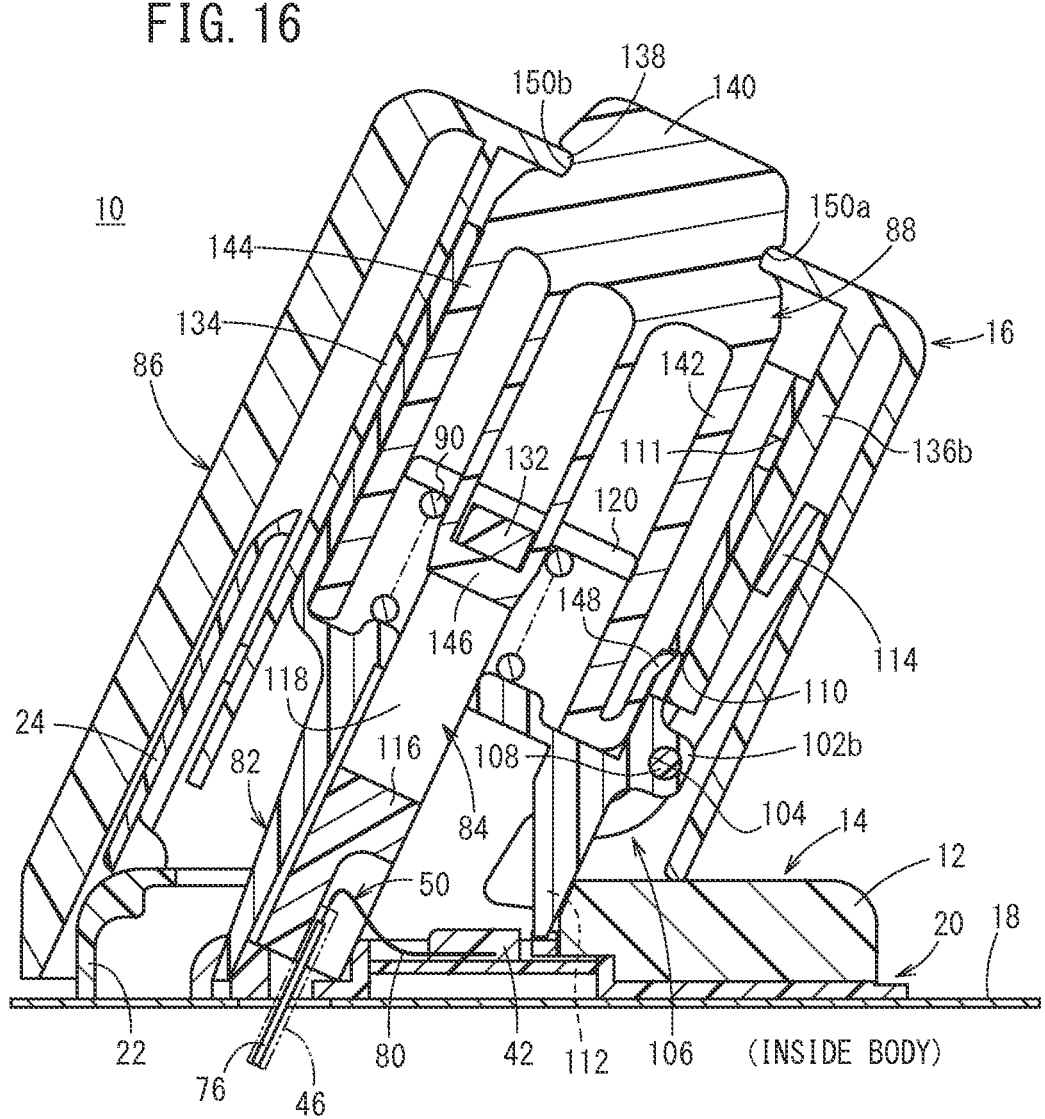
FIG. 16 is a vertical cross-sectional view of the sensor insertion device illustrating a state in which the movement mechanism is displaced toward the body of a subject and the coil spring is compressed.

Then, an operator (mainly, a subject himself/herself) grips the grip member 86, and pushes down the grip member 86 along the guide member 82 as illustrated in FIG. 16. That is, the grip member 86 is displaced toward the body of the subject. Along with this, the pusher 88 engaged with the grip member 86 is also displaced. Since the lock by the safety bar 106 has been already released as described above, the displacement is easily performed.

The entrance portion 146 of the pusher 88 abuts on the stopper 132 of the needle holder 84. Thus, the needle holder 84 is also displaced in the same direction as the displacement direction of the grip member 86 and the pusher 88 along with the displacement of the pusher 88. Thus, the insertion needle 46 held by the needle holding portion 116 of the needle holder 84 and the detection element 76 housed inside the insertion needle 46 move toward the body of the subject. That is, the insertion needle 46 and the detection element 76 pass through the insertion opening 48 (refer to FIG. 3) of the base plate 20 so as to be inserted into the body of the subject. Further, the folded portion 148 is disengaged from the second locking window 111, and the coil spring 90 is compressed.

As the grip member 86 is displaced, the spreading portion 98 of the guide member 82 is gradually housed inside the grip member 86. Thus, the spreading portion 98 is pushed toward the guide member 82 by the inner wall of the grip member 86. As a result, a force in a direction away from the engagement recesses 36 acts on the engagement projections 100 formed on the tip of the spreading portion 98. Therefore, as the grip member 86 is displaced, the engagement projections 100 gradually move away from the engagement recesses 36.

Figure 17:
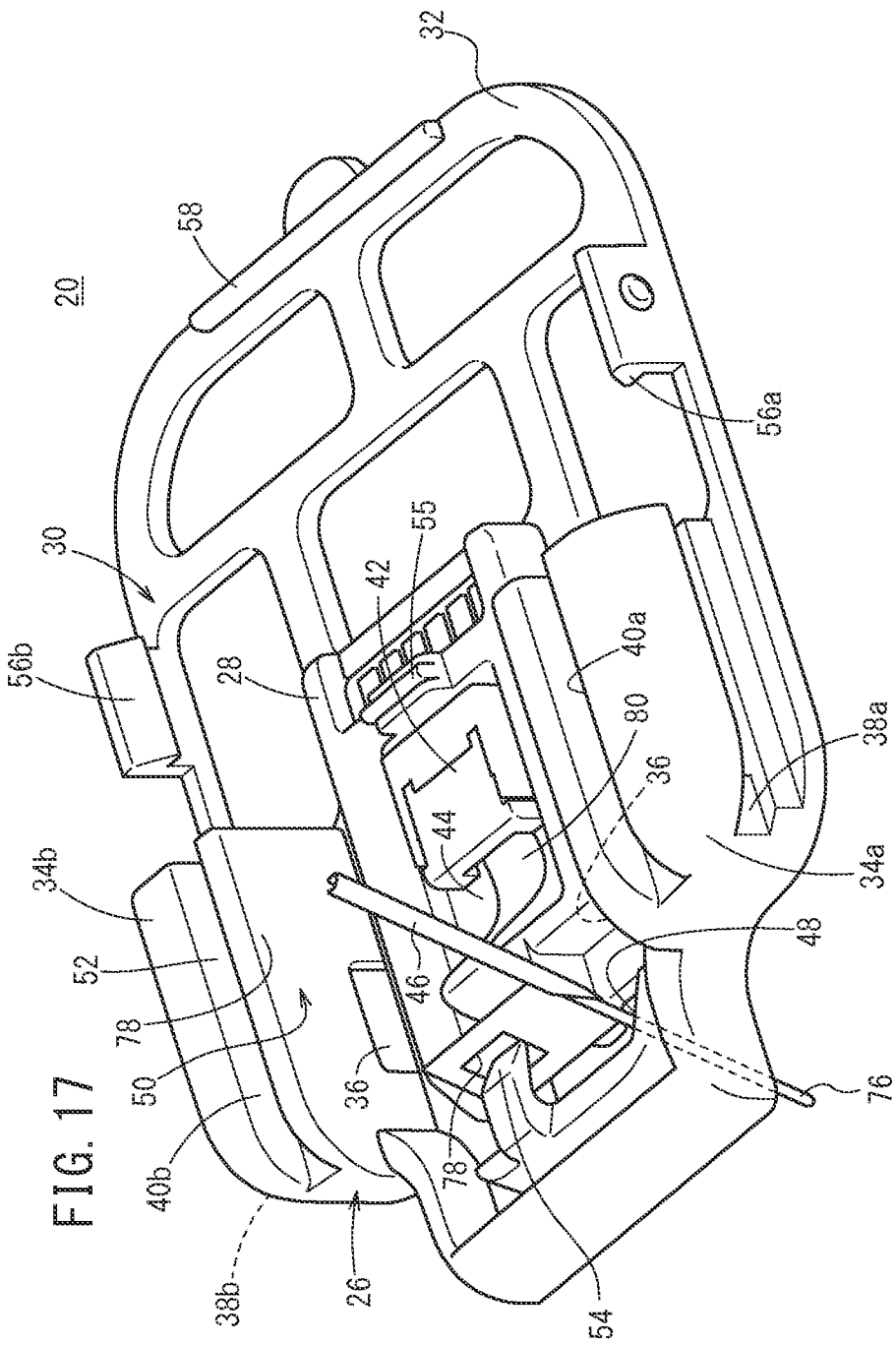
FIG. 17 is a schematic perspective view illustrating the base plate in the positional relationship when a catching portion disposed on the base plate catches the sensor.

When the grip member 86 reaches the displacement end point, the displacement of the pusher 88 and the needle holder 84 finishes, and the insertion of the insertion needle 46 and the detection element 76 also finishes. At this point, the position of the hole 78 of the sensor base 52 is aligned with the catching claw 54 of the device body 14 (base plate 20), and, as illustrated in FIG. 17, the tip of the catching claw 54 passes through the hole 78.

Accordingly, the sensor base 52 is positioned and fixed to the device body 14. This prevents the detection element 76 from coming off the body, and also prevents the flexible cable 80 from being twisted.

At the same time, the engagement projections 100 formed on the tip of the spreading portion 98 of the guide member 82 move away from the engagement recesses 36. As a result, the engagement of the guide member 82 with the device body 14 is released, and the movement mechanism 16 is detached from the device body 14.

When the grip member 86 reaches the displacement end point, the entrance portion 146 climbs over the stopper 132 disposed on the needle holder 84. That is, the entrance portion 146 enters the slit 130 (refer to FIG. 16).

Figure 18:
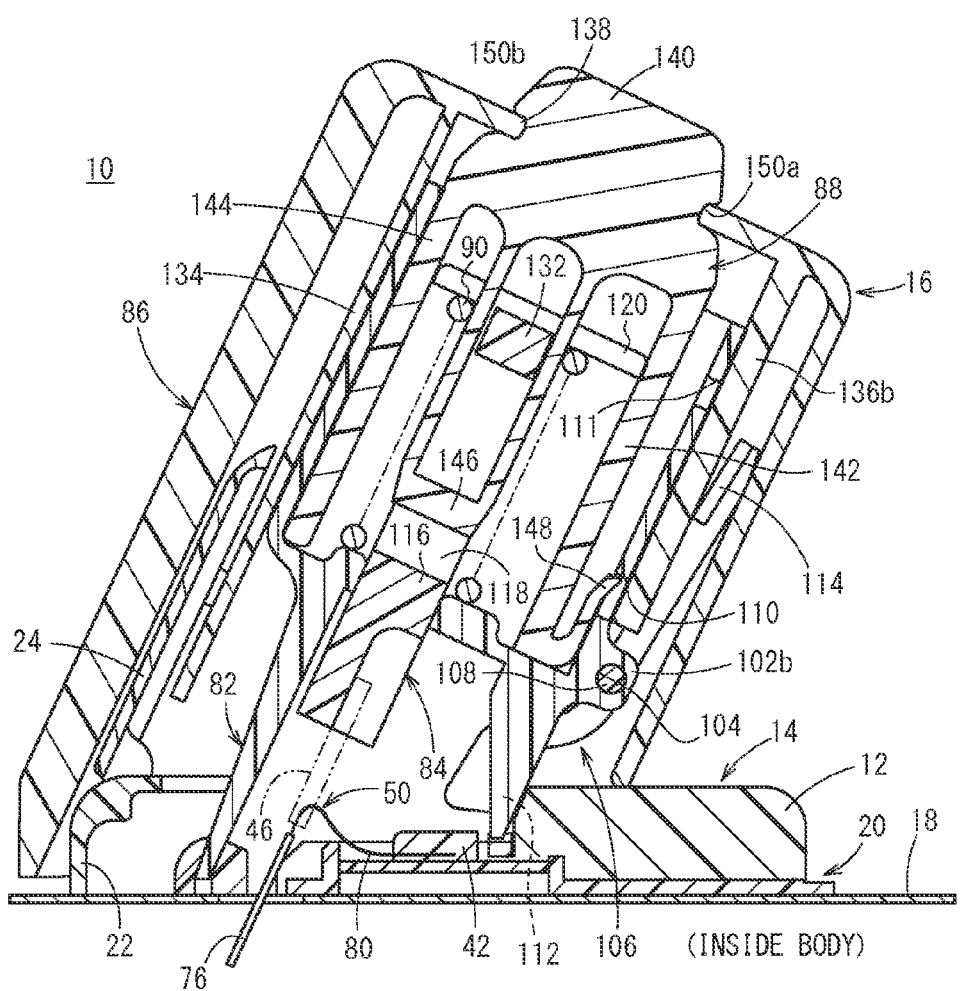
FIG. 18 is a vertical cross-sectional view of the sensor insertion device illustrating a state in which the coil spring extends and the needle holding member is displaced in a direction away from the body of the subject.

Along with this, the needle holder 84 is released from the pushing by the pusher 88. Thus, as illustrated in FIG. 18, the compressed coil spring 90 stretches to return to its original shape. At this point, the coil spring 90 elastically biases the needle holder 84. As a result, the needle holder 84 is displaced obliquely upward along the guide member 82, that is, in a direction away from the device body 14. Along with this, the insertion needle 46 is also displaced obliquely upward. Thus, the insertion needle 46 is taken out of the body of the subject. FIG. 17 illustrates the state at this point.

The sensor base 52 is held by the catching claw 54 as described above. This prevents movement of the sensor 50 and also coming-off of the detection element 76 from the body of the subject along with the displacement of the needle holder 84.

Further, the folded portion 148 of the pusher 88 is locked on the first locking window 110 of the guide member 82. That is, the pusher 88 is engaged with the guide member 82.

Figure 19:
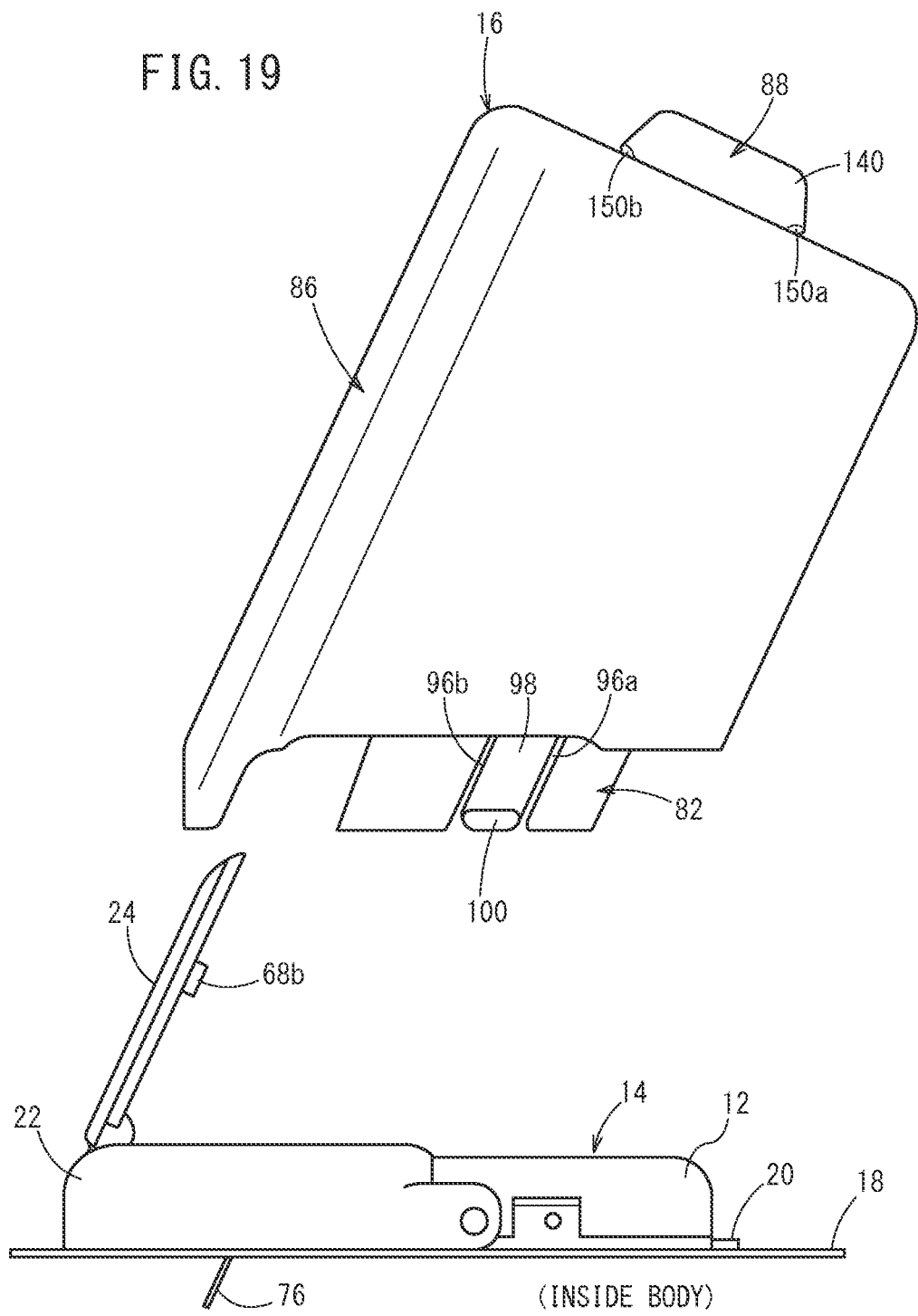
FIG. 19 is a principal part schematic perspective view illustrating a state in which the movement mechanism is detached from the device body.

Then, as illustrated in FIG. 19, the movement mechanism 16 is integrally detached from the device body 14 by the release of the engagement of the guide member 82 with the device body 14, the engagement of the pusher 88 with the guide member 82, and the displacement of the needle holder 84 in the direction away from the device body 14. In other words, in the first embodiment, it is possible to release the safety mechanism, to insert the detection element 76 of the sensor 50 into the body of a subject, and to detach the movement mechanism 16 from the device body 14 while retaining only the device body 14 on the body merely by performing the simple operation of attaching the transmitter 12 to the device body 14, and then gripping and pushing down the grip member 86 toward the body. Therefore, even a person unfamiliar with the sensor insertion device 10 is not likely to perform an erroneous operation.

As described above, the first embodiment makes it possible to prevent an operator from erroneously performing the sensor insertion operation. Therefore, there is less burden on a subject.

In addition, the safety bar 106 is not detached from the movement mechanism 16, but remains integrated with the movement mechanism 16. Thus, there is also an advantage in that the number of waste products does not increase.

In addition, the needle holder 84 is displaced upward in the movement mechanism 16 detached from the device body 14. Thus, the insertion needle 46 is housed inside the guide member 82. This prevents the insertion needle 46 from being stuck in an operator who handles the detached movement mechanism 16 or a surrounding person. That is, it is possible to prevent erroneous sticking of the insertion needle 46.

Along with the detachment of the movement mechanism 16 from the device body 14, the lid member 24 housed inside the grip member 86 is exposed. The lid member 24 is turned around the locking shafts 64a and 64b so as to be a closed state to thereby block the opening of the housing 22. At this point, the hooking claws 68a and 68b (refer to FIG. 5) are hooked on the ceiling wall of the housing 22.

Then, an analyte (e.g., glucose or pH, cholesterol, or protein) in the blood or body fluid of the subject is detected by the detection element 76. A result detected by the detection element 76 is transmitted, as a signal, from the sensor base 52 to the connector 42 through the flexible cable 80. Further, the signal is received by the transmitter 12 through the electrode 70, converted into information, and wirelessly transmitted to the external medical device (specifically, a display device or an electronic medical recording system) automatically or by an operation.

The biological information of the subject can be obtained in the above manner.

Next, a sensor insertion device according to a second embodiment will be described. In elements that correspond to the elements of the sensor insertion device 10 according to the first embodiment, regions having the same functions will be designated by the same reference numerals.

Figure 20:
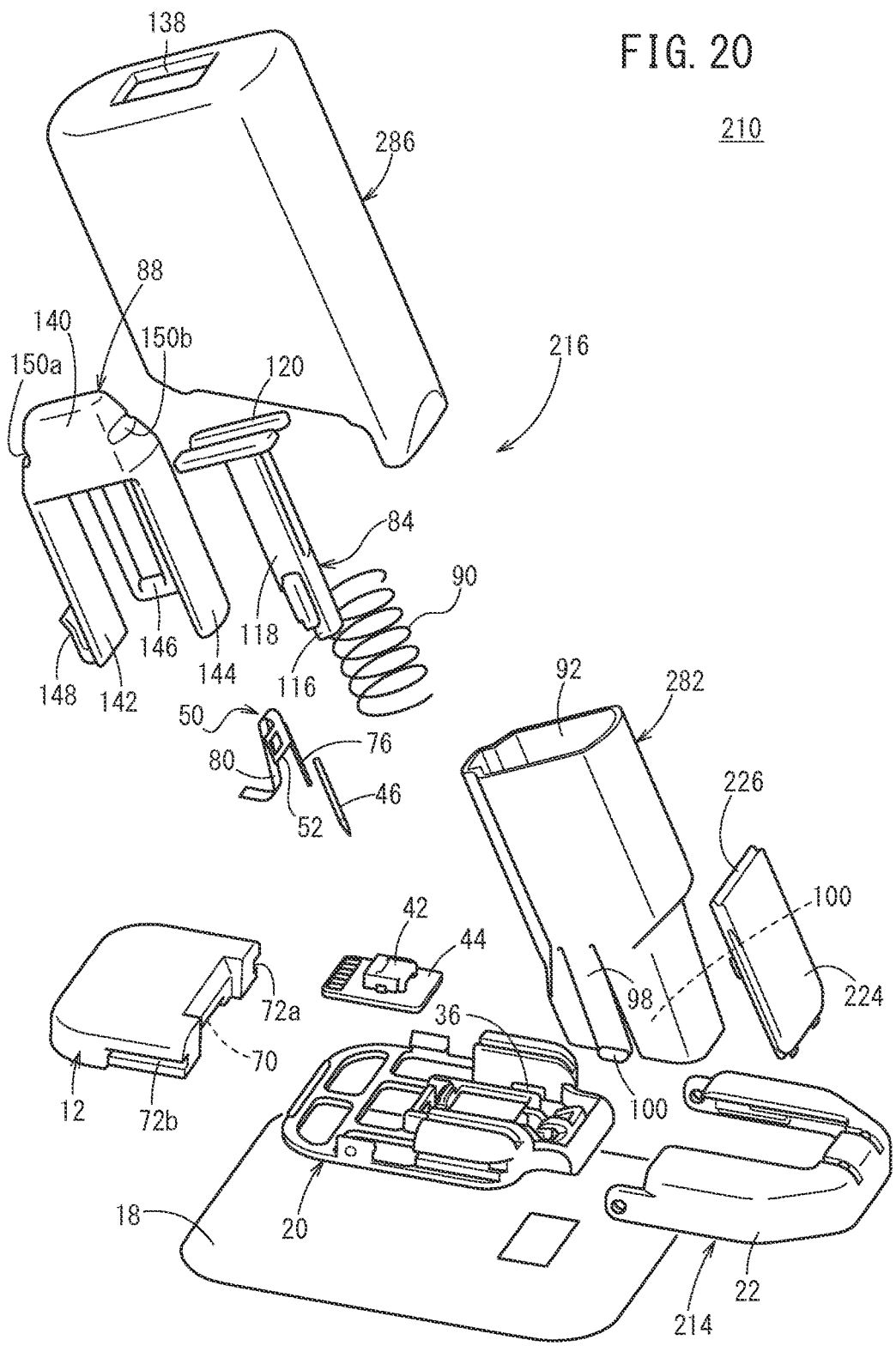
FIG. 20 is an exploded perspective view of a sensor insertion device according to a second embodiment of the present invention.

FIG. 20 is an exploded perspective view of a sensor insertion device 210 according to the second embodiment. The sensor insertion device 210 is provided with a device body 214 to which a transmitter 12 (refer to FIG. 2) is attached and a movement mechanism 216. The sensor insertion device 210 is stuck at an appropriate position on the skin S of a patient (subject) to be used with an adhesive member 18 interposed therebetween in the same manner as in the sensor insertion device 10.

First, the device body 214 will be described. The device body 214 includes a base plate 20, a housing 22 which is attached to the base plate 20, and a lid member 224 which blocks an opening of the housing 22.

Figure 21:
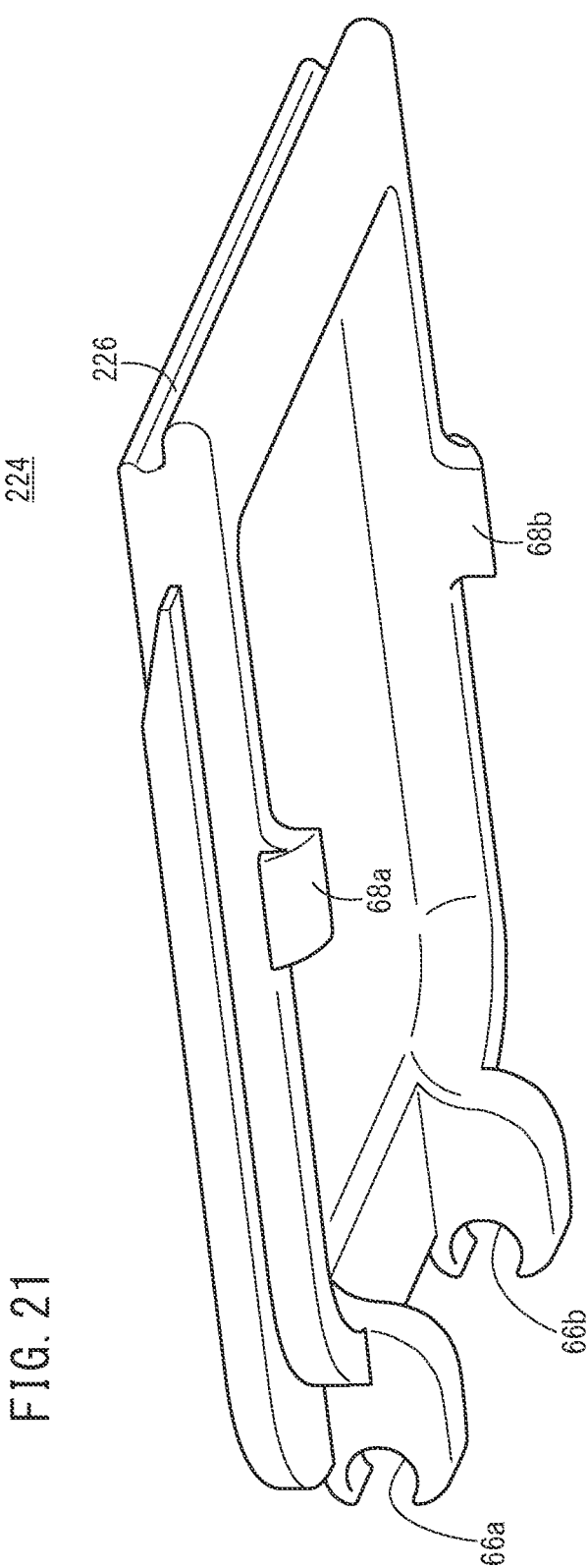
FIG. 21 is a schematic perspective view of a lid member of a device body of the sensor insertion device according to the second embodiment viewed from the lower side.

As illustrated in FIG. 21, a blocking recess 226 is formed in a depressed form on one end of the lid member 224. As is the case with the lid member 24, circular arc-like recesses 66a and 66b into which locking shafts 64a and 64b of the housing 22 are respectively inserted are formed on the other end of the lid member 224, and hooking claws 68a and 68b which project vertically downward are formed on the lower end face of the lid member 24.

That is, the lid member 224 is also turnably locked to the housing 22 by respectively inserting the locking shafts 64a and 64b into the circular arc-like recesses 66a and 66b. Further, when the lid member 224 is in a closed state, the hooking claws 68a and 68b are hooked on a ceiling wall of the housing 22.

The movement mechanism 216 is used for moving a detection element 76 of a sensor 50 illustrated in FIG. 20 together with an insertion needle 46 so as to be inserted into the body of a subject.

The movement mechanism 216 will be specifically described. The movement mechanism 216 includes a guide member 282 which is engageable with the device body 214, a needle holder 84 (needle holding member) which pushes the insertion needle 46 to move, a grip member 286 which is gripped by an operator, a pusher 88 (pushing member) which pushes the needle holder 84, and a coil spring 90 (resilient member) which elastically biases the needle holder 84.

The guide member 282 is configured conforming to the guide member 82 excepting that the shaft support portions 102a and 102b illustrated in FIGS. 8 and 9 are not provided. Thus, regions that are the same as the respective regions of the guide member 82 will be designated by the same reference numerals, and description thereof will be omitted.

Figure 22:
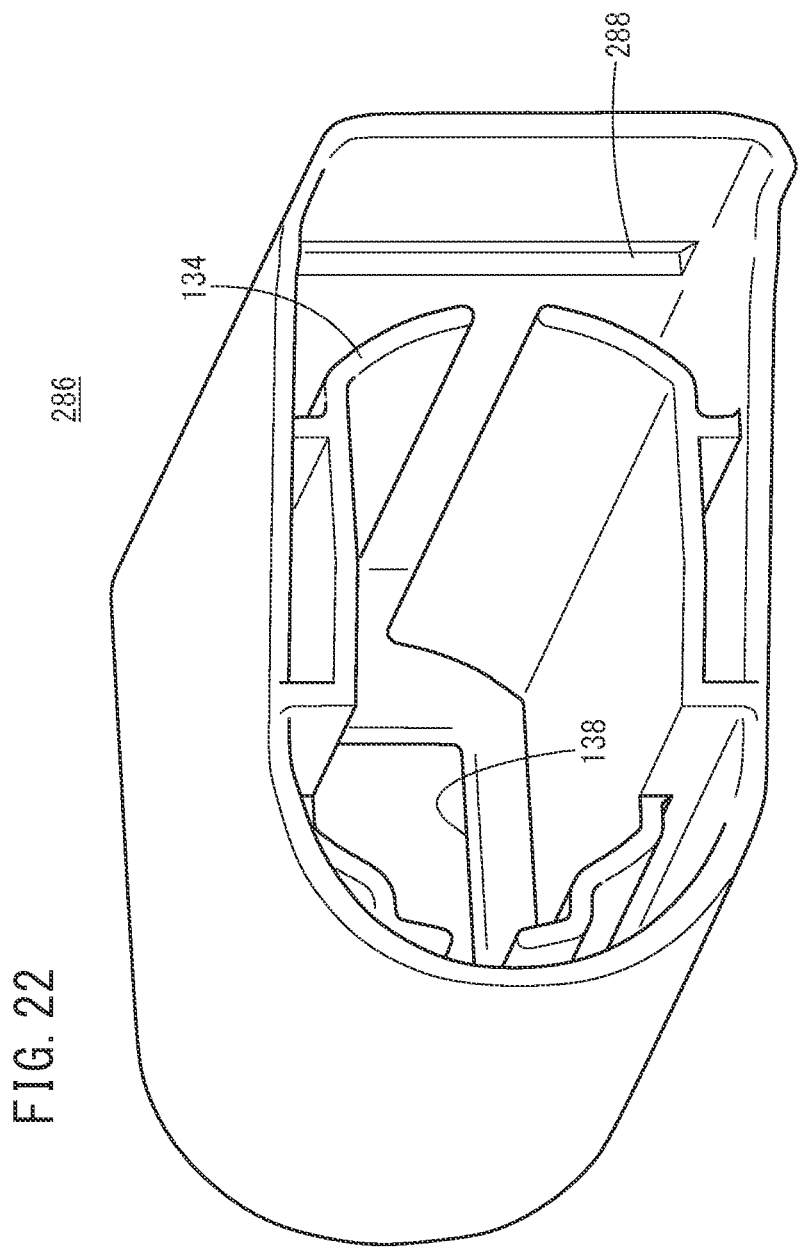
FIG. 22 is a principal part schematic perspective view of a grip member of a movement mechanism of the sensor insertion device according to the second embodiment viewed from the lower side.
Figure 23:
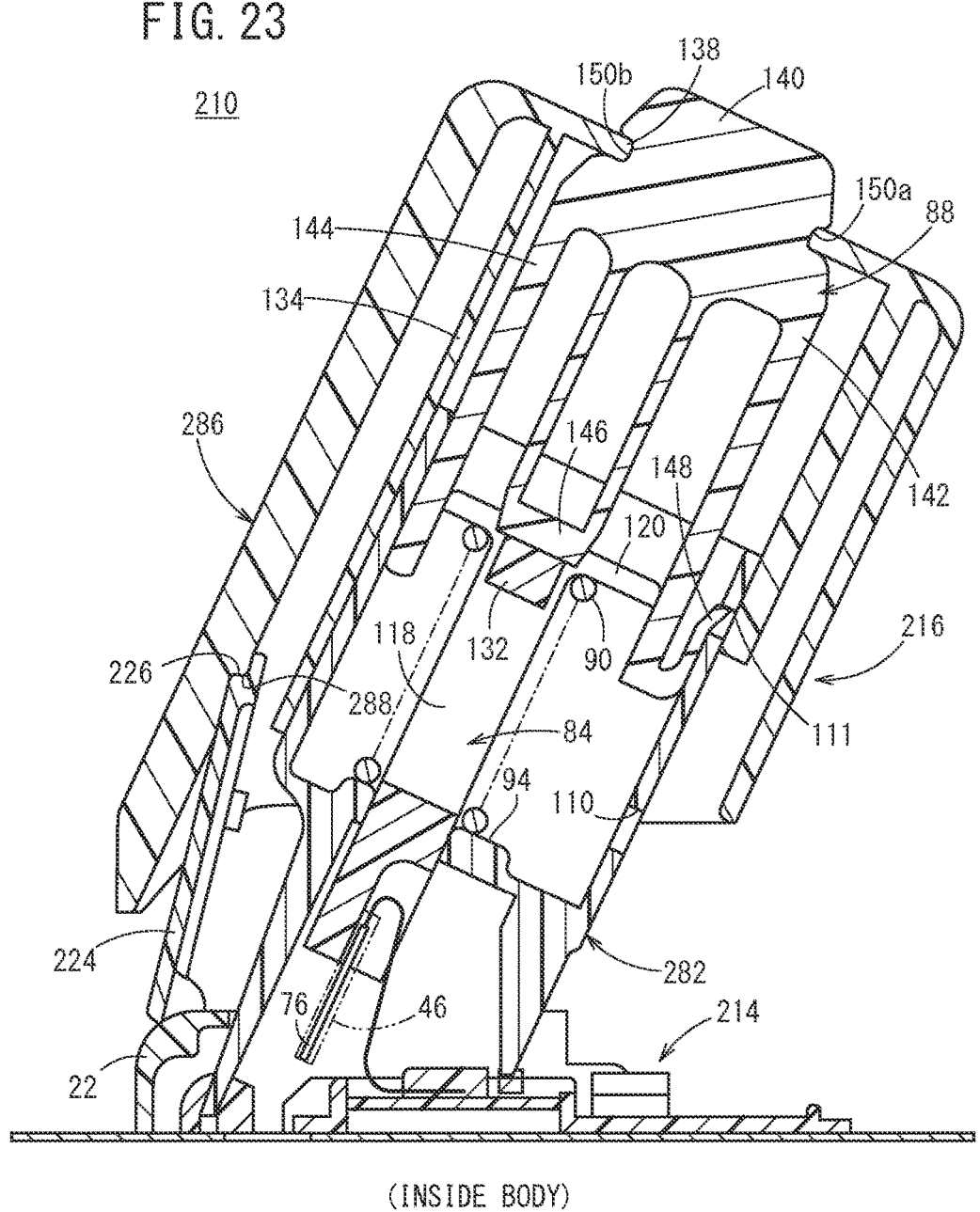
FIG. 23 is a vertical cross-sectional view of the sensor insertion device according to the second embodiment before a transmitter is attached to the device body.

As illustrated in FIGS. 22 and 23, a step portion 288 is formed by notching a part of the inner wall of a long inclined face of the grip member 286. As can be understood from FIG. 23, the step portion 288 enters the blocking recess 226 (refer to FIG. 21) formed on the end of the lid member 224. This entrance brings the grip member 286 into a locked state so that the grip member 286 cannot be displaced toward the body of the subject.

Further, a surrounding wall 134 for surrounding and thereby holding the guide member 282 is formed inside the grip member 286. Further, an engagement hole 138 is formed in a penetrating manner on a flat upper end face of the grip member 286.

For the elements other than those descried above, the same elements as those of the sensor insertion device 10 according to the first embodiment are employed. Thus, those elements will be designated by the same reference numerals as in the first embodiment, and description thereof will be omitted.

Next, effects of the sensor insertion device 210 according to the second embodiment will be described in relation with an operation thereof (sensor insertion method).

Figure 24:
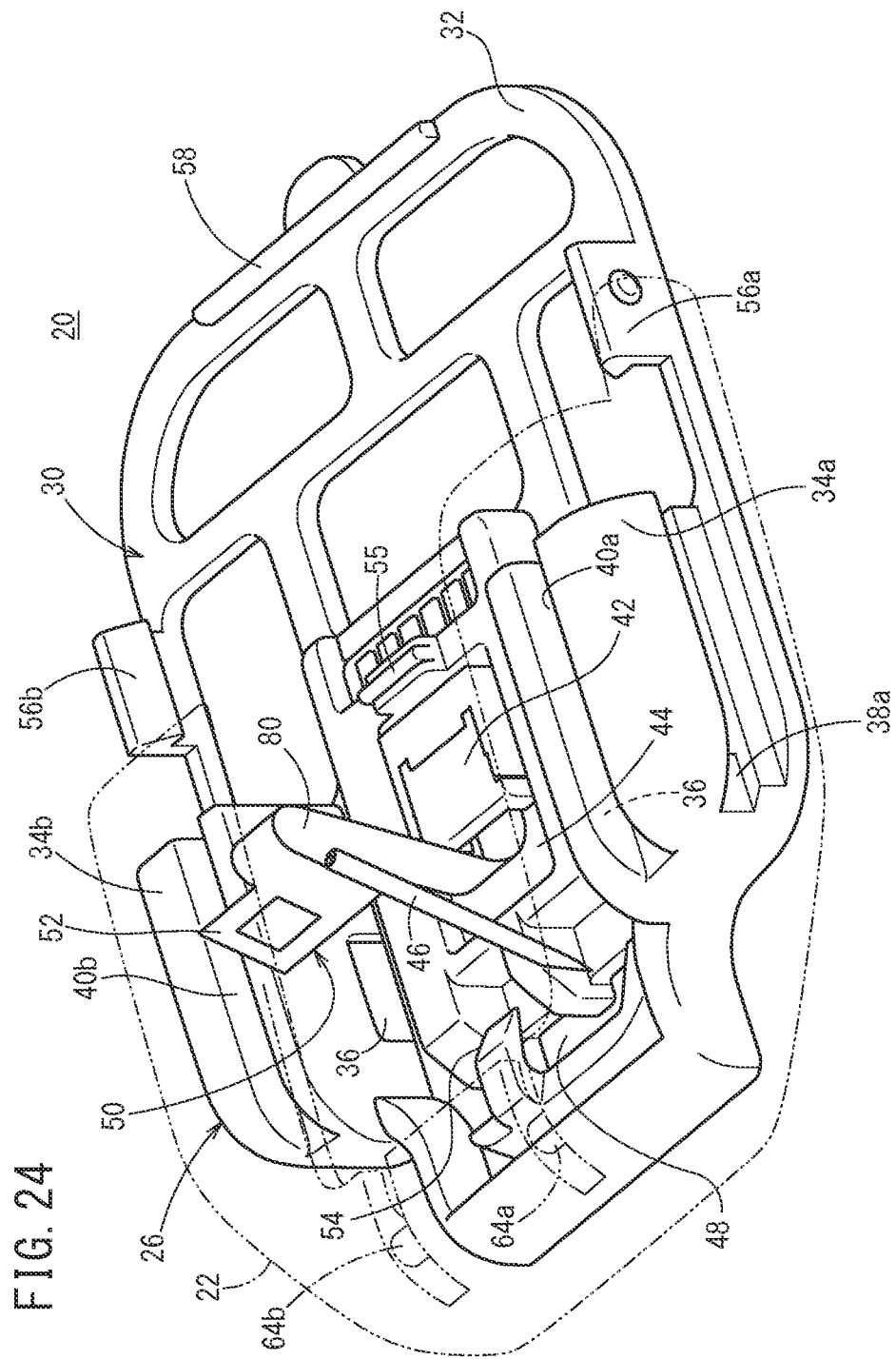
FIG. 24 is a principal part schematic perspective view illustrating the positional relationship between a base plate and a housing in the device body before the transmitter is attached to the device body.

Before the transmitter 12 is attached to the device body 214, as illustrated in FIG. 24, the housing 22 is slidably held by the base plate 20 in such a manner that the rear end face of the housing 22 slightly projects from standing portions 34*a* and 34*b*. That is, first prisms 60*a* and 60*b* (refer to FIG. 3) are slidably inserted into first insertion grooves 38*a* and 38*b*, respectively. Further, second prisms 62*a* and 62*b* are slidably inserted into second insertion grooves 40*a* and 40*b*, respectively.

In this state, the blocking recess 226 of the lid member 224 enters the step portion 288 of the grip member 286 (refer to FIG. 23). This entrance allows the grip member 286 to be blocked by the lid member 224 and brings the grip member 286 into a locked state so that the grip member 286 cannot be displaced toward the body of a subject. That is, it is not possible to insert the detection element 76 into the body of a subject without attaching the transmitter 12 thereto.

In this manner, the lid member 224 functions as a displacement preventing member in the second embodiment. Thus, it is possible to prevent an erroneous operation of inserting the insertion needle 46 and the detection element 76 without attaching the transmitter 12 thereto.

In this state, the transmitter 12 is attached to the device body 214. Specifically, grasping claws 56*a* and 56*b* are respectively inserted into grooves 72*a* and 72*b* to be grasped which are formed on opposite side parts of the transmitter 12. Then, in this state, the transmitter 12 is allowed to slide toward a first attachment portion 26.

During the slide, the tip face of the transmitter 12 comes into contact with the rear end face of the housing 22 because the rear end face of the housing 22 slightly projects from the standing portions 34*a* and 34*b* as described above (refer to FIG. 24).

Figure 25:
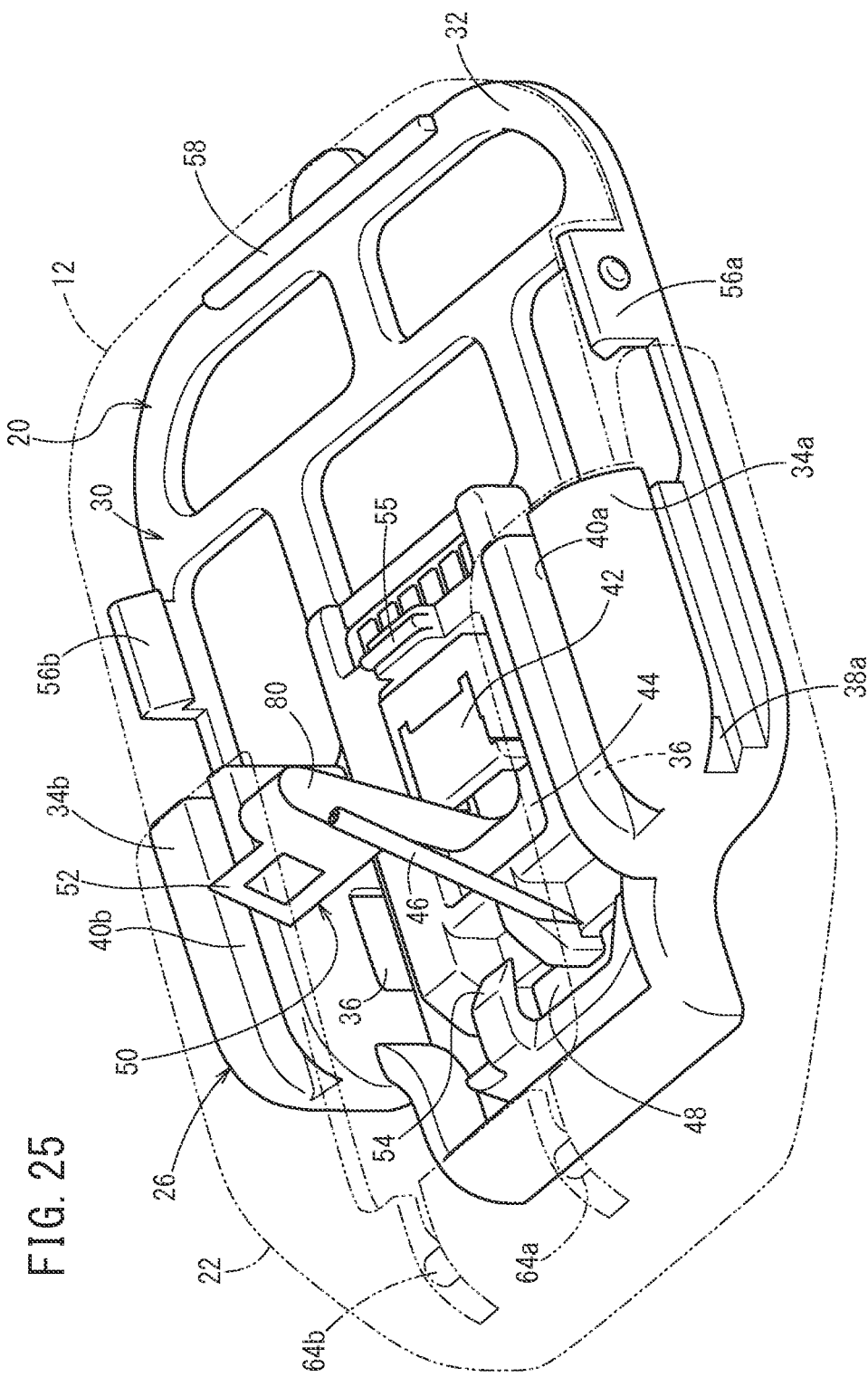
FIG. 25 is a principal part schematic perspective view illustrating the positional relationship between the base plate, the housing, and the transmitter when the transmitter is attached to the device body and the housing is moved forward (displaced) from the state of FIG. 24.

Thus, the housing 22 is pushed by the sliding transmitter 12, and moves forward (displaced) in a direction away from a second attachment portion 30. The displacement of the housing 22 and the slide of the transmitter 12 finish when the tip face of the transmitter 12 comes into contact with the rear end faces of the standing portions 34*a* and 34*b* and a blocking portion 58 which is disposed on the base plate 20 enters an entrance recess 74 (refer to FIG. 6) of the transmitter 12 as illustrated in FIG. 25.

Along with the displacement of the housing 22, the lid member 224 in which the locking shafts 64*a* and 64*b* of the housing 22 are respectively inserted into the circular arc-like recesses 66*a* and 66*b* turns to be inclined toward the housing 22. As a result, as illustrated in FIG. 26, the blocking recess 226 is disengaged from the step portion 288, and the blocked state of the grip member 286 is released to release the locked state.

Then, a release paper stuck on the lower end face of an adhesive member 18 is peeled off, and the adhesive member 18 is stuck at an appropriate position on the skin S of the patient. Accordingly, the sensor insertion device 210 is positioned on the skin S.

Then, an operator (mainly, a subject himself/herself) grips the grip member 286, and pushes down the grip member 286 along the guide member 282. Along with this, the pusher 88 which is engaged with the grip member 286 is also displaced. Since the lock of the grip member 286 by the lid member 224 has been already released as described above, the displacement is easily performed.

Thereafter, the same operations as performed in the first embodiment are performed. Specifically, an entrance portion 146 of the pusher 88 abuts on a stopper 132 of the needle holder 84. Thus, the needle holder 84 is also displaced in the same direction as the displacement direction of the grip member 286 and the pusher 88 along with the displacement of the pusher 88. Thus, the insertion needle 46 held by a needle holding portion 116 of the needle holder 84 and the detection element 76 housed inside the insertion needle 46 move toward the body of the subject. That is, the insertion needle 46 and the detection element 76 pass through an insertion opening 48 (refer to FIG. 24) of the base plate 20 so as to be inserted into the body of the subject. Further, a folded portion 148 of the pusher 88 is disengaged from a second locking window 111 of the guide member 282, and the coil spring 90 is compressed.

As the grip member 286 is displaced, a spreading portion 98 of the guide member 282 is gradually housed inside the grip member 286. Thus, the spreading portion 98 is pushed toward the guide member 282 by the inner wall of the grip member 286. As a result, a force in a direction away from engagement recesses 36 acts on engagement projections 100 formed on the tip of the spreading portion 98. Therefore, as the grip member 286 is displaced, the engagement projections 100 gradually move away from the engagement recesses 36.

When the grip member 286 reaches a displacement end point, the displacement of the pusher 88 and the needle holder 84 finishes, and the insertion of the insertion needle 46 and the detection element 76 also finishes. At this point, the position of a hole 78 to be caught of a sensor base 52 is aligned with a catching claw 54 of the device body 214 (base plate 20), and, in the same manner as illustrated in FIG. 17, the tip of the catching claw 54 passes through the hole 78.

Accordingly, the sensor base 52 is positioned and fixed to the device body 214. This prevents the detection element 76 from coming off the body, and also prevents a flexible cable 80 from being twisted.

At the same time, the engagement projections 100 formed on the tip of the spreading portion 98 of the guide member 282 move away from the engagement recesses 36. As a result, the engagement of the guide member 282 with the device body 214 is released, and the movement mechanism 216 is detached from the device body 214.

When the grip member 286 reaches the displacement end point, the entrance portion 146 climbs over the stopper 132 disposed on the needle holder 84. That is, the entrance portion 146 enters a slit 130.

Along with this, the needle holder 84 is released from the pushing by the pusher 88. Thus, in the same manner as illustrated in FIG. 18, the compressed coil spring 90 stretches to return to its original shape. At this point, the coil spring 90 elastically biases the needle holder 84. As a result, the needle holder 84 is displaced obliquely upward along the guide member 282, that is, in a direction away from the device body 214. Along with this, the insertion needle 46 is also displaced obliquely upward. Thus, the insertion needle 46 is taken out of the body of the subject.

The sensor base 52 is held by the catching claw 54 as described above. This prevents movement of the sensor 50 and also coming-off of the detection element 76 from the body of the subject along with the displacement of the needle holder 84.

Further, the folded portion 148 of the pusher 88 is locked on a first locking window 110 of the guide member 282. That is, the pusher 88 is engaged with the guide member 282.

Then, in the same manner as illustrated in FIG. 19, the movement mechanism 216 is integrally detached from the device body 214 by the release of the engagement of the guide member 282 with the device body 214, the engagement of the pusher 88 with the guide member 282, and the displacement of the needle holder 84 in the direction away from the device body 214. In other words, also in the second embodiment, it is possible to release the safety mechanism, to insert the detection element 76 of the sensor 50 into the body of a subject, and to detach the movement mechanism 216 from the device body 214 while retaining only the device body 214 on the body merely by performing the simple operation of attaching the transmitter 12 to the device body 214, and then gripping and pushing down the grip member 286 toward the body. Therefore, even a person unfamiliar with the sensor insertion device 210 is not likely to perform an erroneous operation. Further, since the insertion needle 46 is housed inside the guide member 282, it is possible to prevent erroneous sticking of the insertion needle 46.

As described above, the second embodiment makes it possible to prevent an operator from erroneously performing the sensor insertion operation as is the case with the first embodiment. In addition, since the lid member 224 constitutes a part of the device body 214, there is also an advantage in that the number of waste products does not increase.

Along with the detachment of the movement mechanism 216 from the device body 214, the lid member 224 housed inside the grip member 286 is exposed. The lid member 224 is turned around the locking shafts 64a and 64b so as to be a closed state to thereby block the opening of the housing 22. At this point, the hooking claws 68a and 68b (refer to FIG. 5) are hooked on the ceiling wall of the housing 22.

Then, an analyte (e.g., glucose or pH, cholesterol, or protein) in the blood or body fluid of the subject is detected by the detection element 76. A result detected by the detection element 76 is transmitted, as a signal, from the sensor base 52 to a connector 42 through the flexible cable 80. Further, the signal is received by the transmitter 12 through an electrode 70, converted into information, and wirelessly transmitted to the external medical device (specifically, a display device or an electronic medical recording system) automatically or by an operation.

The present invention is not particularly limited to the above embodiments, and various modifications may be made without departing from the gist of the invention.

For example, the transmitter 12 may be attached after the sensor insertion device 10 or 210 is positioned on the skin S.

What is claimed is:

1. A sensor insertion device for inserting a detection element of a sensor configured to measure biological information of a subject into the body of the subject, the sensor insertion device comprising:
    a device body;
    a data process unit attached to the device body, the data process unit being configured to process a signal that includes biological information detected by the detection element;
    a movement mechanism detachably attached to the device body, the movement mechanism being configured to move the detection element together with an insertion needle configured to be stuck into the body of the subject to insert the detection element and the insertion needle into the body of the subject, the movement mechanism comprising:
        a hollow guide member that is engageable with the device body,
        a needle holding member configured to push the insertion needle to move inside the guide member,
        a grip member configured to be gripped by an operator,
        a pushing member held by the grip member, the pushing member being configured to be displaced along with displacement of the grip member along the guide member, and the pushing member being configured to push the needle holding member, and
        a resilient member configured to bias the needle holding member in a direction away from the device body; and
    a displacement preventing member configured (i) to block the grip member and thereby prevent displacement of the movement mechanism toward to the body of the subject when the data processor is not attached to the device body, and (ii) move under pushing action of the data process unit to release the blockage of the grip member when the data process unit is attached to the device body,
    wherein the sensor insertion device is configured such that insertion needle is movable into the body of the subject when the pushing member is displaced along with displacement of the grip member toward the body of the subject and the pushing member pushes the needle holding member,
    wherein the sensor insertion device is configured such that, when the pushing member reaches a displacement end point, the pushing member, remaining held by the grip member, engages with the guide member,
    wherein the sensor insertion device is configured such that, when the grip member and the pushing member reach the displacement end point, the guide member is released from engagement with the device body by the grip member, and
    wherein the sensor insertion device is configured such that, when the grip member and the pushing member reach the displacement end point, the needle holding member is displaced in a direction away from the device body by an action of the resilient member.

2. The sensor insertion device according to claim 1, wherein the displacement preventing member is a bar-like member that is attached to the guide member and is configured to be directly pushed by the data process unit.

3. The sensor insertion device according to claim 1, wherein the device body includes:
    a base plate;
    a housing attached to the base plate; and
    a lid member attached to the housing and configured to block an opening of the housing.

4. The sensor insertion device according to claim 3, wherein the displacement preventing member is the lid member, and
    wherein the lid member is configured to move when the base plate is pushed by the data process unit.

5. The sensor insertion device according to claim 1, wherein the needle holding member is an elongated member that has a slit extending along a longitudinal direction of the needle holding member,
    wherein a stopper is disposed in the slit of the needle holding member,
    wherein the pushing member has an entrance portion that is configured to interact with the stopper and to be disposed in the slit, and
    wherein the sensor insertion device is configured such that when the entrance portion is pushed past the stopper and is disposed in the slit, the needle holding member is displaced in the direction away from the device body under an action of the resilient member.

6. The sensor insertion device according to claim 1,
wherein an engagement portion of the guide member configured to be engaged with the device body is formed on the tip of a spreading portion of the guide member that spreads outward from the guide member, and
wherein the spreading portion is configured such that the spreading portion is pushed by an inner wall of the grip member when the grip member is displaced toward the device body and the engagement portion is disengaged from the device body when the grip member reaches the displacement end point.

7. The sensor insertion device according to claim 1, wherein a holding wall configured to hold the resilient member is formed inside the guide member.

8. The sensor insertion device according to claim 1, wherein the device body includes a catching portion configured to engage the sensor when the needle holding member reaches the displacement end point.

9. The sensor insertion device according to claim 1, wherein the data process unit is a transmitter.

10. A method for inserting a detection element of a sensor configured to measure biological information of a subject into a body of the subject, the method comprising:
providing a movement mechanism detachably attached to a device body, the movement mechanism comprising:
a hollow guide member that is engageable with the device body,
a needle holding member configured to push an insertion needle to move inside the guide member,
a grip member configured to be gripped by an operator,
a pushing member held by the grip member, the pushing member being configured to be displaced along with displacement of the grip member, and the pushing member being configured to push the needle holding member,
a resilient member configured to bias the needle holding member in a direction away from the device body;
disposing a displacement preventing member to block the grip member and prevent displacement of the movement mechanism toward the body of the subject;
placing the device body, to which the movement mechanism is attached by engagement of a guide member, in contact with the body of the subject;
attaching a data process unit to the device body such that the data process unit pushes the displacement preventing member to a position that unblocks the grip member;
displacing the pushing member that is held by the grip member to push the needle holding member so as to to stick the insertion needle into the body of the subject and move the sensor; and
moving the grip member, the pushing member, and the needle holding member to a displacement end point, thereby (i) engaging the pushing member with the guide member, (ii) releasing the guide member from engagement with the device body by the grip member, and (iii) causing intiation of displacement of the needle holding member in a direction away from the device body by an action of the resilient member such that the detection element is implanted inside the body.

11. The sensor insertion method according to claim 10, wherein the displacement preventing member is a bar-like member attached to the guide member, and the bar-like member is directly pushed by the data process unit.

12. The sensor insertion method according to claim 10,
wherein the device body includes a base plate, a housing attached to the base plate, and a lid member attached to the housing configured to block an opening of the housing, and
wherein the displacement preventing member is the lid member and the lid member is moved when the the base plate is moved by pushing the base plate with the data process unit.

13. The sensor insertion method according to claim 10,
wherein the needle holding member is an elongated member that has a slit extending along the longitudinal direction of the needle holding member,
wherein a stopper is disposed in the slit of the needle holding member,
wherein the pushing member has an entrance portion that is configured to interact with the stopper and to be disposed in the slit, and
wherein when the entrance portion is pushed past the stopper and is disposed in the slit, the needle holding member is displaced in the direction away from the device body under an action of the resilient member.

14. The sensor insertion method according to claim 10,
wherein an engagement portion of the guide member configured to be engaged with the device body is formed on the tip of a spreading portion of the guide member that spreads outward from the guide member, and
wherein the spreading portion is configured such that the spreading portion is pushed by an inner wall of the grip member when the grip member is displaced toward the device body and the engagement portion is disengaged from the device body when the grip member reaches the displacement end point.

15. The sensor insertion method according to claim 10, wherein the device body includes a catching portion configured to engage the sensor when the needle holding member reaches the displacement end point.

* * * * *